(12) United States Patent
Hashimoto et al.

(10) Patent No.: US 7,162,930 B2
(45) Date of Patent: Jan. 16, 2007

(54) ULTRASONIC SENSOR

(75) Inventors: Masahiko Hashimoto, Shijonawate (JP); Hidetomo Nagahara, Kyoto (JP); Masaaki Suzuki, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/510,348

(22) PCT Filed: Apr. 28, 2003

(86) PCT No.: PCT/JP03/05436

§ 371 (c)(1),
(2), (4) Date: Oct. 6, 2004

(87) PCT Pub. No.: WO2004/098234

PCT Pub. Date: Nov. 11, 2004

(65) Prior Publication Data

US 2005/0139013 A1 Jun. 30, 2005

(51) Int. Cl.
*G01F 1/66* (2006.01)

(52) U.S. Cl. .................................. 73/861.25

(58) Field of Classification Search ............ 73/861.27, 73/861.26, 861.28, 861.29, 861.31, 861.25; 367/152
See application file for complete search history.

(56) References Cited

U.S. PATENT DOCUMENTS 4,063,214 A 12/1977 Kritz
4,336,719 A * 6/1982 Lynnworth ............... 73/861.27
4,552,021 A * 11/1985 Miwa et al. .................. 73/644
5,437,194 A * 8/1995 Lynnworth ............... 73/861.27
5,531,124 A 7/1996 Kim et al.
6,634,239 B1 * 10/2003 Gomm et al. ............ 73/861.27
6,776,051 B1 * 8/2004 Suzuki et al. ............ 73/861.27
6,854,338 B1 * 2/2005 Khuri-Yakub et al. ... 73/861.27

FOREIGN PATENT DOCUMENTS

| EP | 1237148 | 9/2002 |
|---|---|---|
| GB | 925541 | 5/1963 |
| GB | 1555549 | 11/1979 |
| JP | 52-73763 | 6/1977 |
| JP | 1-246998 | 10/1989 |
| JP | 6-101880 | 12/1994 |
| JP | 9-33307 | 2/1997 |
| JP | 9-065477 | 3/1997 |
| JP | 2000-298045 | 10/2000 |
| JP | 2000-298047 | 10/2000 |
| JP | 2000-304581 | 11/2000 |

* cited by examiner

*Primary Examiner*—Jewel Thompson
(74) *Attorney, Agent, or Firm*—Wenderoth, Lind & Ponack, L.L.P.

(57) ABSTRACT

There are provided an ultrasonic transducer that performs transmission and/or reception of an ultrasonic wave, and a propagation medium portion that forms a propagation path of the ultrasonic wave. A density and an acoustic velocity of the propagation medium portion, and a density and a sound velocity of a fluid that fills a circumjacent space are appropriately set, and a propagation loss of the ultrasonic wave into the fluid is reduced to almost zero by refracting the ultrasonic wave at an appropriate angle.

30 Claims, 14 Drawing Sheets

ULTRASONIC SENSOR

TECHNICAL FIELD

The present invention relates to an ultrasonic sensor for transmitting or receiving an ultrasonic wave, and more precisely, to an ultrasonic transmitter for transmitting an ultrasonic wave, an ultrasonic receiver for receiving an ultrasonic wave, or an ultrasonic transmitter-receiver for either or both of them receiving and transmitting an ultrasonic wave.

BACKGROUND ART

In recent years, ultrasonic transmitter-receivers have been industrially utilized in a wide variety of fields of distance measurement, object detection, flow measurement, robot control and the like.

As a first ultrasonic transmitter-receiver, there is the ultrasonic transmitter-receiver described in Japanese Examined Patent Publication No. 6-101880. Construction and operation of this conventional ultrasonic transmitter-receiver will be described with reference to FIG. 10.

FIG. 10 is a sectional view of a first conventional ultrasonic transmitter-receiver. In FIG. 10, reference numeral 100 denotes an ultrasonic transmitter-receiver, 101 an ultrasonic transducer, 102 an acoustic matching layer, and 103 a housing.

In the construction of FIG. 10, operation during wave transmission will be described first. The ultrasonic transducer 101 receives a drive signal given from a drive circuit (transmitter circuit 701) via signal wires 104 and generally generates ultrasonic vibrations at a frequency in the vicinity of a resonance frequency of the ultrasonic transducer 101. The ultrasonic vibrations generated at the ultrasonic transducer 101 are transmitted to a fluid around the ultrasonic transmitter-receiver 100 via the acoustic matching layer 102. The acoustic matching layer 102 is constructed of a material having acoustic impedance intermediate an acoustic impedance of a circumjacent fluid and an acoustic impedance of the ultrasonic transducer 101, and has a function to improve wave transmission efficiency to the circumjacent fluid.

A piezoelectric ceramic is typically used for the ultrasonic transducer 101 that generates ultrasonic vibrations, and its acoustic impedance is, for example, about $30 \times 10^6$ $kg \cdot m^{-2} \cdot s^{-1}$. When the circumjacent fluid is a gas of air or the like, the acoustic impedance of, for example, air is about 400 $kg \cdot m^{-2} \cdot s^{-1}$, the acoustic impedance of the acoustic matching layer 102 is set to about $0.11 \times 10^6$ $kg \cdot m^{-2} \cdot s^{-1}$, and a thickness is preferably set to a quarter of a wavelength at an estimated ultrasonic frequency.

Conventionally, in order to form a matching layer that has an acoustic impedance intermediate those of the piezoelectric transducer and air, there is used a material obtained by solidifying a material (for example, glass balloons or plastic balloons) of a comparatively small density with resin.

Operation during ultrasonic wave reception will be described next. An ultrasonic wave, which has propagated through the circumjacent fluid and reached the ultrasonic transmitter-receiver 100, is transmitted to the ultrasonic transducer 101 via the acoustic matching layer 102 conversely to ultrasonic wave transmission. The ultrasonic transducer 101 converts a dynamic action of the ultrasonic wave into an electric signal, and the signal is transmitted to an electric processing section (not shown) via the signal wires 104.

During these transmission and reception operations of the ultrasonic transmitter-receiver 100 described above, transmission and reception of an ultrasonic wave are effected in a direction in which the ultrasonic transducer 101 and the acoustic matching layer 102 are laminated, i.e., in a perpendicular direction of the acoustic matching layer 102.

As a second conventional ultrasonic transmitter-receiver, there is, for example, the ultrasonic transmitter-receiver laid open in the ultrasonic flowmeter described in Japanese Unexamined Patent Publication No. 2000-304581. Construction and operation of this conventional ultrasonic transmitter-receiver will be described below with reference to FIG. 11.

FIG. 11 is a sectional view of a second conventional ultrasonic transmitter-receiver. In FIG. 11, 104 denotes a first acoustic matching layer and 105 a second acoustic matching layer. The first acoustic matching layer 104 has a structure in which a plurality of layers of material plates (104a, 104b, 104c, . . . ) differing in density and acoustic velocity are laminated and these materials are laminated in a descending order of magnitude of acoustic velocity.

Operation of the ultrasonic transmitter-receiver 100 in the construction of FIG. 11 will be described below. During wave transmission, an ultrasonic wave generated by the ultrasonic transducer 101 propagates through the first acoustic matching layer 104 (104a, 104b, 104c, . . . ) and enters the second acoustic matching layer 105 by a drive signal applied from signal wires (not shown). A time during which the ultrasonic wave passes through each layer (104a, 104b, 104c, . . . ) of the laminated first acoustic matching layer 104 is set so as to become equalized, and a wave front of the ultrasonic wave coincides at an interface between the first acoustic matching layer 104 and the second acoustic matching layer 105. That is, the wave propagates in a perpendicular direction at an interface to the first acoustic matching layer 104 in the second acoustic matching layer 105.

The ultrasonic wave, which has propagated through the second acoustic matching layer 105, is refracted by a difference in acoustic velocity between the second acoustic matching layer 105 and an interface of a circumjacent fluid, and radiated to the circumjacent fluid with a direction thereof changed.

During wave reception, the ultrasonic wave, which has propagated through the circumjacent fluid and reached the ultrasonic transmitter-receiver 100 through a process reverse to wave transmission, is refracted at the interface to the second acoustic matching layer 105 to enter the second acoustic matching layer 105, and converted into an electric signal by the ultrasonic transducer 101 via the first acoustic matching layer 104. In this case, an acoustic wave arriving from a direction of wave transmission is selectively received.

The second conventional ultrasonic transmitter-receiver, which can integrate the ultrasonic transmitter-receiver with a wall of a measurement channel when being applied to an ultrasonic flowmeter, since the direction of the acoustic wave is changed by utilizing refraction, therefore has an advantage in that no disorder of flow of the fluid to be measured is generated.

However, there has been an issue in that a propagation loss has inevitably occurred and efficiency of wave transmission and reception has been reduced even if a matching layer of a low density, like the first conventional ultrasonic transmitter-receiver, is used when propagating an ultrasonic wave from an ultrasonic transducer of piezoelectric ceramic or the like into a gas of air or the like. A reason why it is difficult to make an ultrasonic wave efficiently propagate from a solid to a gas is that acoustic impedance of the gas is much smaller than acoustic impedance of the solid, and a strong reflection of an ultrasonic wave disadvantageously occurs at an interface even if a matching layer is interposed.

Further, an ultrasonic transmitter-receiver of a type that effects deflection of an ultrasonic wave utilizing refraction exhibited by the second conventional ultrasonic transmitter-receiver has had an issue in that it has not substantially been applicable as a consequence of a significant reduction in wave transmission and reception efficiency when an angle of deflection is increased due to an additionally inflicted loss caused by the angle of deflection.

Accordingly, the present invention is made in view of the aforementioned issues and has an object of providing a highly sensitive ultrasonic sensor that can deflect an ultrasonic wave and has a high efficiency of wave transmission and reception.

SUMMARY OF THE INVENTION

In order to achieve the aforementioned object, the present invention is constructed as follows.

According to the present invention, there is provided an ultrasonic sensor for performing transmission or reception of an ultrasonic wave to a circumjacent space filled with a fluid, the sensor comprising:

an ultrasonic transducer; and a propagation medium portion that is filled in a space between the ultrasonic transducer and the circumjacent space, for forming a propagation path of the ultrasonic wave.

Further, according to the present invention, there is provided an ultrasonic sensor for performing transmission or reception of an ultrasonic wave to a circumjacent space filled with a fluid, the sensor comprising:

an ultrasonic transducer; and a propagation medium portion that is arranged between the ultrasonic transducer and the circumjacent space, for forming a propagation path of the ultrasonic wave, wherein a density $\rho_1$ of the propagation medium portion, an acoustic velocity $C_1$ in the propagation medium portion, a density $\rho_2$ of the fluid that fills the space, and a sound velocity $C_2$ in the fluid that fills the space satisfy a relation expressed as $(\rho_2/\rho_1)<(C_1/C_2)<1$.

According to the present invention, there is also provided an ultrasonic sensor for performing transmission or reception of an ultrasonic wave to a circumjacent space filled with a fluid, the sensor comprising:

an ultrasonic transducer;

a propagation medium portion that is arranged between the ultrasonic transducer and the circumjacent space, for forming a propagation path of the ultrasonic wave; and a reflector that is arranged in contact with the propagation medium portion, for controlling the propagation path of the ultrasonic wave, wherein a density $\rho_1$ of the propagation medium portion, an acoustic velocity $C_1$ in the propagation medium portion, a density $\rho_2$ of the fluid that fills the space, and a sound velocity $C_2$ in the fluid that fills the space satisfy a relation expressed as $(\rho_2/\rho_1)<(C_1/C_2)<1$.

According to the present invention, there is provided an ultrasonic flowmeter comprising:

a flow measurement section having an inner wall that defines a channel of a fluid to be measured;

at least one ultrasonic transducer that is provided outside a channel space enclosed by the inner wall of the flow measurement section, for performing transmission or reception of an ultrasonic wave; and a propagation medium portion that is arranged between the at least one ultrasonic transducer and the channel space, for forming a propagation path of the ultrasonic wave, wherein a density $\rho_1$ of the propagation medium portion, an acoustic velocity $C_1$ in the propagation medium portion, a density $\rho_2$ of the fluid to be measured, and a sound velocity $C_2$ of the fluid to be measured satisfy a relation expressed as $(\rho_2/\rho_1)<(C_1/C_2)<1$.

According to another aspect of the present invention, there is provided an ultrasonic flowmeter comprising:

a flow measurement section having an inner wall that defines a channel of a gas;

a pair of ultrasonic transducers that are provided outside a channel space enclosed by the inner wall of the flow measurement section, for performing transmission or reception of an ultrasonic wave; and a pair of propagation medium portions that are arranged between each of the pair of ultrasonic transducers and the channel space, for refracting a propagation path of the ultrasonic wave, with each propagation medium portion comprising a first surface region that faces an ultrasonic vibration surface of a corresponding ultrasonic transducer, and a second surface region that faces the channel space, and with the first surface region of the propagation medium portion being inclined in a direction of flow velocity of the gas in the channel space, and the second surface region being almost parallel to a direction of flow velocity of the gas in the channel space.

According to another aspect of the present invention, there is provided an ultrasonic sensor for performing transmission or reception of an ultrasonic wave to a circumjacent space filled with a fluid, the sensor comprising:

an ultrasonic transducer; and a propagation medium portion that is filled in a space between the ultrasonic transducer and the circumjacent space, for forming a propagation path of the ultrasonic wave, wherein the propagation medium portion has a first surface region that faces an ultrasonic vibration surface of the ultrasonic transducer, and a second surface region that faces a flow filling the circumjacent space, and the second surface region of the propagation medium portion is inclined with respect to the first surface region.

BRIEF DESCRIPTION OF DRAWINGS

These and other aspects and features of the present invention will become clear from the following description taken in conjunction with the preferred embodiments thereof with reference to the accompanying drawings, in which.

DETAILED DESCRIPTION OF THE PREFERRED EMBODIMENTS

Figure 1A:
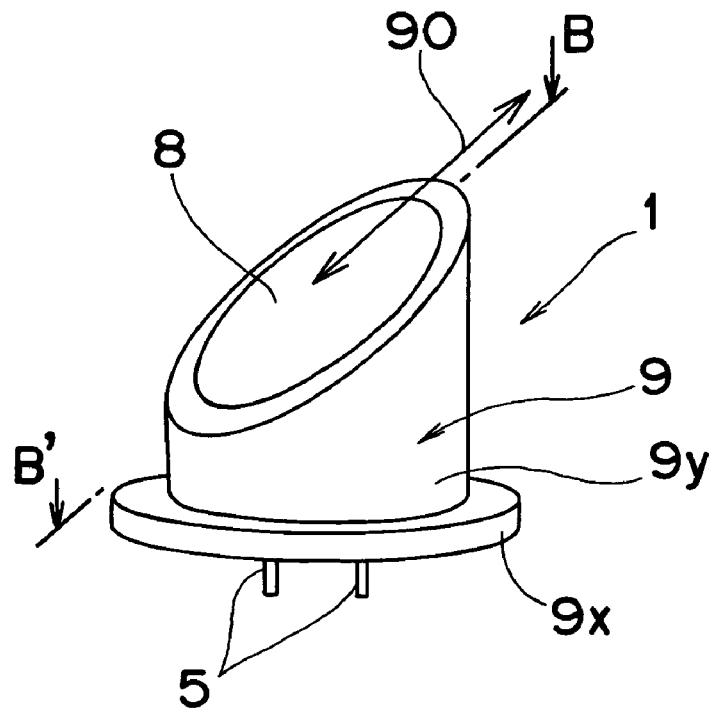
FIG. 1A is a perspective general view of an ultrasonic transmitter-receiver according to a first embodiment of the present invention.

Before description of the present invention proceeds, it is to be noted that like parts are designated by like reference numerals throughout the accompanying drawings.

Before describing preferred embodiments of the present invention below with reference to the drawings, various aspects of the present invention are described in advance.

According to a first aspect of the present invention, there is provided an ultrasonic sensor for performing transmission or reception of an ultrasonic wave to or from a circumjacent space filled with a fluid, the sensor comprising:

au ultrasonic transducer; and a propagation medium portion that is filled in a space between the ultrasonic transducer and the circumjacent space, for forming a propagation path of the ultrasonic wave.

According to a second aspect of the present invention, there is provided an ultrasonic sensor for performing transmission or reception of an ultrasonic wave to or from a circumjacent space filled with a fluid, the sensor comprising:

an ultrasonic transducer; and a propagation medium portion that is arranged between the ultrasonic transducer and the circumjacent space, for forming a propagation path of the ultrasonic wave, wherein a density $\rho_1$ of the propagation medium portion, an acoustic velocity $C_1$ in the propagation medium portion, a density $\rho_2$ of the fluid that fills the space, and a sound velocity $C_2$ in the fluid that fills the space satisfy a relation expressed as $(\rho_2/\rho_1)<(C_1/C_2)<1$.

According to a third aspect of the present invention, there is provided the ultrasonic sensor as defined in the second aspect, wherein the propagation medium portion has a first surface region that faces an ultrasonic vibration surface of the ultrasonic transducer and a second surface region that faces a flow that fills the circumjacent space, and the second surface region of the propagation medium portion is inclined with respect to the first surface region.

According to a fourth aspect of the present invention, there is provided an ultrasonic sensor for performing transmission or reception of an ultrasonic wave to or from a circumjacent space filled with a fluid, the sensor comprising:

an ultrasonic transducer;

a propagation medium portion that is arranged between the ultrasonic transducer and the circumjacent space, for forming a propagation path of the ultrasonic wave; and a reflector that is arranged in contact with the propagation medium portion, for controlling the propagation path of the ultrasonic wave, wherein a density $\rho_1$ of the propagation medium portion, an acoustic velocity $C_1$ in the propagation medium portion, a density $\rho_2$ of the fluid that fills the space, and a sound velocity $C_2$ in the fluid that fills the space satisfy a relation expressed as $(\rho_2/\rho_1)<(C_1/C_2)<1$.

According to a fifth aspect of the present invention, there is provided the ultrasonic sensor as defined in the fourth aspect, wherein the propagation medium portion has a first surface region that faces an ultrasonic vibration surface of the ultrasonic transducer, a second surface region that faces a flow that fills the circumjacent space, and at least one third surface region that is arranged between the first surface region and the second surface region in the propagation path of the ultrasonic wave and brought in contact with the reflector, and the second surface region of the propagation medium portion is inclined with respect to at least one of the first surface region and the third surface region.

According to a sixth aspect of the present invention, there is provided the ultrasonic sensor as defined in any one of the first through fifth aspects, wherein a density $\rho_1$ of the propagation medium portion, an incident angle $\theta_1$ of an ultrasonic wave relative to a direction normal to an interface between the propagation medium portion and the fluid that fills the circumjacent space, a density $\rho_2$ of the fluid that fills the circumjacent space, and an approach angle $\theta_2$ of the ultrasonic wave relative to the direction normal to the interface between the propagation medium portion and the fluid that fills the circumjacent space almost satisfy a relation expressed as $\rho_2/\rho_1 = \cot\theta_2/\cot\theta_1$.

According to a seventh aspect of the present invention, there is provided the ultrasonic sensor as defined in any one of the first through fifth aspects, wherein the propagation medium portion is formed of a dry gel of an inorganic oxide or an organic polymer.

According to an eighth aspect of the present invention, there is provided the ultrasonic sensor as defined in the sixth aspect, wherein a solid frame portion of the dry gel is made hydrophobic.

According to a ninth aspect of the present invention, there is provided the ultrasonic sensor as defined in the seventh aspect, wherein a density of the dry gel is not greater than 500 kg/m$^3$, and a mean pore diameter of the dry gel is not greater than 100 nm.

According to a tenth aspect of the present invention, there is provided the ultrasonic sensor as defined in any one of the first through fifth aspects, comprising: an acoustic matching layer that is provided between the ultrasonic transducer and the propagation medium portion, for acoustically matching the ultrasonic transducer with the propagation medium portion.

According to an eleventh aspect of the present invention, there is provided the ultrasonic sensor as defined in any one of the first through fifth aspects, wherein the fluid that fills the circumjacent space is a gas having a density $\rho_2$ of not greater than 10 kg/m$^3$.

According to a twelfth aspect of the present invention, there is provided the ultrasonic sensor as defined in any one of the first through fifth aspects, wherein a direction of transmission or reception of an ultrasonic wave is almost parallel to the second surface region.

Embodiments of the present invention will be described below.

First Embodiment

An ultrasonic transmitter-receiver as one example of an ultrasonic sensor according to a first embodiment of the present invention will be described in detail below with reference to the drawings.

The present inventor has discovered that an ultrasonic wave can be propagated from a solid to a fluid (particularly, gas) causing almost no loss at an interface if the ultrasonic wave is appropriately refracted by using a propagation medium portion made of an appropriate material in an ultrasonic transmitter-receiver, and then came to consider the present invention.

In the ultrasonic transmitter-receiver according to the first embodiment of the present invention, a propagation medium portion that has a plane (first surface region) parallel to a vibration surface of an ultrasonic transducer and a plane (second surface region) brought into contact with a fluid that fills a circumjacent space is arranged between the ultrasonic transducer and the fluid that fills the circumjacent space. It is to be noted that the term of "fluid that fills the circumjacent space" means a fluid brought into contact with at least the second surface region and does not necessarily mean a fluid that fills an entire periphery of the ultrasonic sensor (for example, the ultrasonic transmitter-receiver) but means a fluid that fills a part of the periphery within the specification and scope of the claims of the present application.

First of all, the ultrasonic transmitter-receiver according to the first embodiment of the present invention will be described with reference to FIGS. 1A and 1B. FIG. 1A shows a perspective general view of ultrasonic transmitter-receiver 1 of the first embodiment, and FIG. 1B shows a sectional view of the ultrasonic transmitter-receiver 1 taken along line B–B' of FIG. 1A.

Figure 1B:
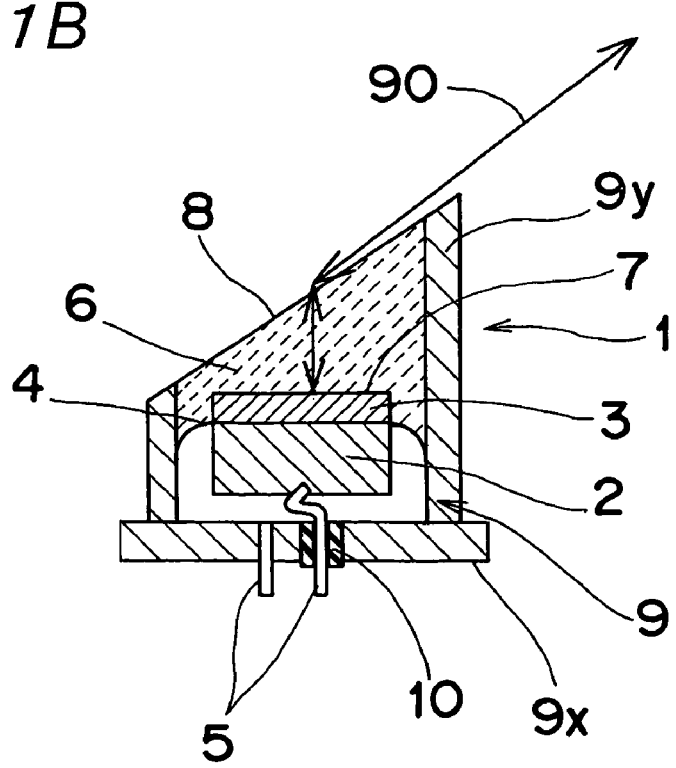
FIG. 1B is a sectional view taken along line B—B of FIG. 1A perpendicular to a lengthwise direction of the ultrasonic transmitter-receiver of the first embodiment.

The ultrasonic transmitter-receiver 1 shown in FIGS. 1A and 1B is provided with: an ultrasonic transducer 2 for converting electric signals into ultrasonic vibrations or converting ultrasonic vibrations into electric signals; a propagation medium portion 6 that is arranged between a fluid in a circumjacent space and the ultrasonic transducer 2 and forms a propagation path of an ultrasonic wave; an acoustic matching layer 3 that is arranged between the ultrasonic transducer 2 and the propagation medium portion 6 and provides matching of acoustic impedance between the ultrasonic transducer 2 and the propagation medium portion 6; a transducer casing 4 that houses therein the ultrasonic transducer 2 and concurrently serves as an electrical conductive path to the ultrasonic transducer 2; an insulating portion 10, arranged at a terminal plate 9x, for preventing electrical short-circuit between two signal wires 5 for providing input and output of signals to the ultrasonic transducer 2; and a housing 9 that houses a part of the two signal wires 5, the ultrasonic transducer 2, the propagation medium portion 6, the acoustic matching layer 3, and the transducer casing 4. The housing 9 is constructed of a cylindrical side portion 9y cut so as to be inclined at a prescribed angle with respect to an axial direction as shown in FIGS. 1A and 1B, and the terminal plate 9x that is fixed to a lower end portion of the side portion 9y and functions as a part of the housing 9.

The propagation medium portion 6 is filled in a space that is enclosed by the housing 9 constructed of the terminal plate 9x and the side portion 9y, located outside the transducer casing 4 and other than the acoustic matching layer 3 arranged inside the space, and has a first surface region 7 which faces the acoustic matching layer 3 and the ultrasonic transducer 2 (note that it directly faces the acoustic matching layer 3) and a second surface region 8 which faces the fluid that fills the circumjacent space. Further, the second surface region 8 of the propagation medium portion 6 is inclined at a prescribed angle with respect to the first surface region 7 so as not to become parallel to the first surface region 7. In this case, the prescribed angle, as one example, is an angle greater than 0° and smaller than 90°, preferably substantially smaller than 80°. In the first embodiment, assuming that a density of the propagation medium portion 6 is $\rho_1$, an acoustic velocity of the propagation medium portion 6 is $C_1$, a density of the fluid that fills the circumjacent space is $\rho_2$ and an acoustic velocity of the fluid that fills the circumjacent space is $C_2$, then a material of the propagation medium portion 6 is selected so as to satisfy the relation expressed by the following expression (1):

$$(\rho_2/\rho_1) < (C_1/C_2) < 1 \tag{1}$$

When the fluid is a gas of air or the like, it is difficult to find a material that satisfies the above-mentioned condition. A reason for the above is that there are few solid materials whose acoustic velocity $C_1$ is smaller than the acoustic velocity $C_2$ of gas. In the first embodiment, in order to provide the propagation medium portion 6 that satisfies the aforementioned condition, the propagation medium portion 6 is formed of a dry gel of an inorganic oxide or an organic polymer. A solid frame portion of the dry gel employed in the first embodiment is made hydrophobic, and a density thereof is not greater than 500 kg/m$^3$. This dry gel is a nano-porous dry gel (nanoporous dry gel) having a mean pore diameter of not greater than 100 nm.

The solid frame portion of the dry gel of the inorganic oxide preferably has an ingredient of at least silicon oxide (silica) or aluminum oxide (alumina). Moreover, the solid frame portion of the dry gel of the organic polymer can be constructed of a general thermosetting resin or a thermoplastic resin. For example, there can be used polyurethane, polyurea, phenol cured resin, polyacrylamide, polymethyl methacrylate, or the like.

In a case where the propagation medium portion 6 is formed of a nanoporous dry gel that has a main ingredient of, for example, silica, if the density $\rho_1$ is 200 kg/m$^3$, then the acoustic velocity $C_1$ can be set within a range of about 100 m/s to 180 m/s. When the fluid that fills the circumjacent space is air, since the density $\rho_2$ of air is 1.22 kg/m$^3$ and the acoustic velocity $C_2$ is 340 m/s, it is possible to concurrently satisfy relations expressed as $\rho_2 < \rho_1$ and $C_1 < C_2$ and satisfy a relation expressed as $(\rho_2/\rho_1) < (C_1/C_2)$ by adopting the above propagation medium portion 6. When measuring a gas such as natural gas, the propagation medium portion 6 preferably has a density $\rho_1$ ranging from 100 to 300 kg/m$^3$ and an acoustic velocity $C_1$ ranging from 100 to 300 m/s.

The ultrasonic transducer 2 is a piezoelectric element and is able to generate an electric signal by generation of ultrasonic vibrations and/or arrival of an ultrasonic wave as a consequence of applying an electric signal. Piezoelectric ceramics are suitably employed as the piezoelectric material. If it is desired to control resonance characteristic and reduce mechanical Q-value, an absorber may be peripherally arranged.

The ultrasonic transmitter-receiver 1 of the first embodiment has a function to improve acoustic matching between the ultrasonic transducer 2, that is an ultrasonic generating source, and the propagation medium portion 6 by providing the acoustic matching layer 3 between the propagation medium portion 6 and the ultrasonic transducer 2.

In a case where the propagation medium portion 6 is formed of the nanoporous dry gel (acoustic impedance: $3 \times 10^4$ kg·m$^{-2}$·s$^{-1}$) having a main ingredient of silica, and the ultrasonic transducer 1 is constructed of a piezoelectric ceramic (acoustic impedance: $30 \times 10^6$ kg·m$^{-2}$·s$^{-1}$), by adopting an acoustic matching layer 3 produced from a material having an acoustic impedance in the vicinity of $1 \times 10^6$ kg·m$^{-2}$·s$^{-1}$, a propagation efficiency of ultrasonic energy can be made to be almost one or concretely not smaller than 0.95. The above material can be provided by a composite material obtained by solidifying a hollow glass ball with a resin material, or a porous ceramic. A thickness of the acoustic matching layer 3 is preferably set to a quarter wavelength of an ultrasonic wave used.

Furthermore, in the ultrasonic transmitter-receiver 1 of the first embodiment, the ultrasonic transducer 2 is housed in the transducer casing 4, while the ultrasonic transducer 2 is bonded to an inside of a top surface of the transducer casing 4, and the acoustic matching layer 3 is bonded to an outside of the top surface of the transducer casing 4, constituting a laminate structure. The transducer casing 4 is preferably formed of a conductive metallic material of stainless steel or the like, and acoustic matching between the ultrasonic transducer 2 and the acoustic matching layer 3 can be maintained in a satisfactory state by thickness setting to a thickness of not greater than 1/10 or preferably not greater than 1/20 of a wavelength of an estimated ultrasonic wave.

The transducer casing 4 is bonded to the terminal plate 9x of the housing 9 by a processing method of electric welding or the like and is able to have a hermetic structure filled with an inert gas of dry nitrogen, argon, or the like. With the above-mentioned arrangement, the ultrasonic transducer 2 is physically insulated from an external air environment, allowing reliability to be improved. In addition, there is provided an electrically shielded structure, and therefore, high safety can be secured even when the fluid that fills the circumjacent space is a flammable fluid of natural gas or the like.

Figure 2:
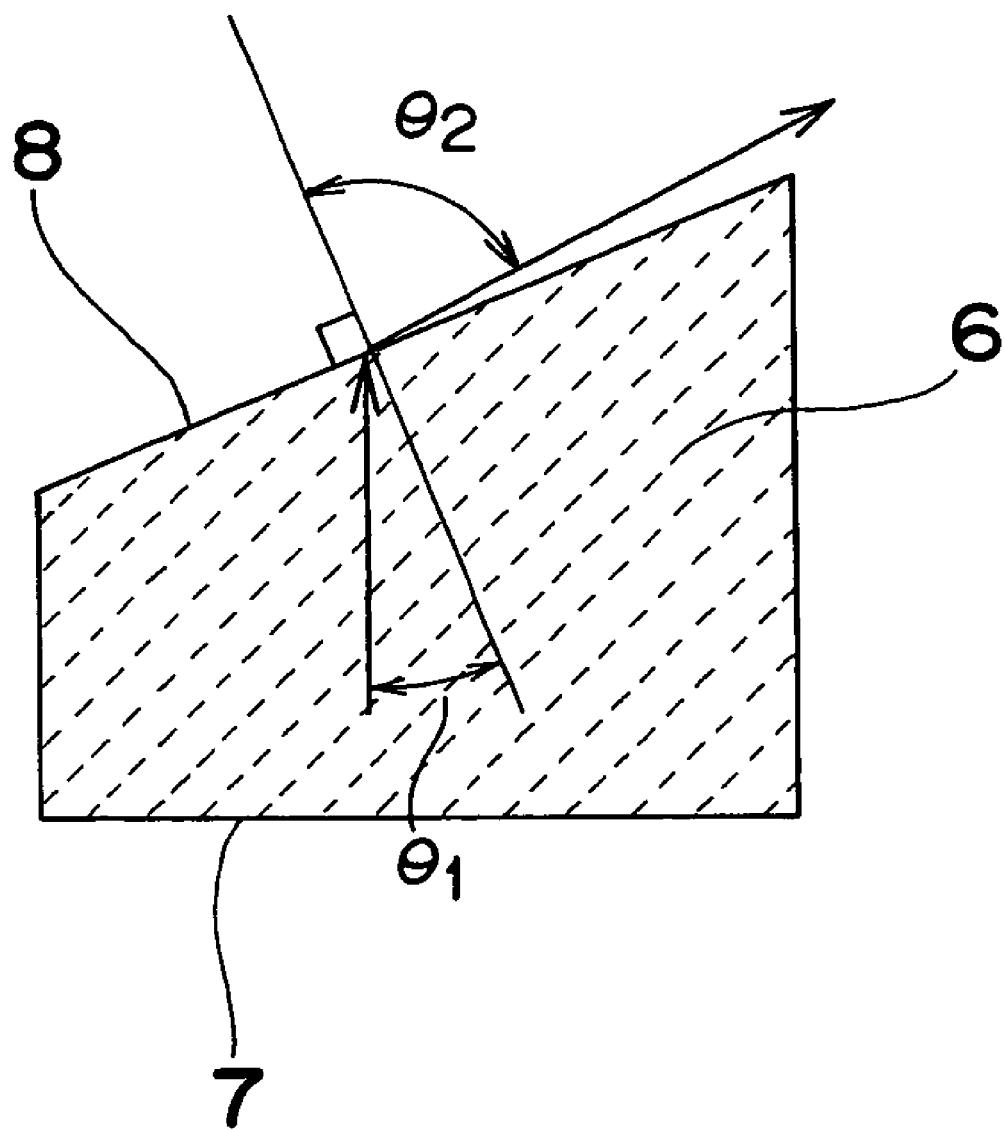
FIG. 2 is a sectional view showing refraction of an ultrasonic wave at an interface between a propagation medium portion of the ultrasonic transmitter-receiver and a fluid in a circumjacent space thereof.

Next, behavior of an ultrasonic wave propagating from the propagation medium portion 6 to the fluid that fills the circumjacent space will be described in detail below with reference to FIG. 2.

According to the aforementioned relationship of arrangement, an ultrasonic wave enters from a normal direction of the first surface region 7 that faces the vibration surface of the ultrasonic transmitter-receiver 1 and is parallel to the vibration surface. Therefore, the ultrasonic wave enters along a direction inclined with respect to a normal direction of the second surface region 8 that is an interface between the propagation medium portion 6 and the fluid that fills the circumjacent space. It is assumed that an incident angle of the ultrasonic wave with respect to the normal direction of the second surface region 8 is $\theta_1$ ($0° < \theta_1 < 90°$). At this time, the ultrasonic wave is refracted at the second surface region 8, that is the interface between the propagation medium portion 6 and the fluid that fills the circumjacent space, and enters the fluid to be measured at an angle $\theta_2$ (approach angle) with respect to the normal direction ($\theta_1 < \theta_2$).

In the first embodiment, various parameters ($\rho_1$, $\theta_1$, and $\theta_2$) are set so as to almost satisfy a relation of the following expression (2) when the density $\rho_2$ of the fluid that fills the circumjacent space is given.

$$(\rho_2/\rho_1) = (\cot \theta_2 / \cot \theta_1) \quad (2)$$

With the above setting, propagation efficiency from the propagation medium portion 6 of ultrasonic energy to the fluid that fills the circumjacent space becomes almost one. At this time, the incident angle $\theta_1$ satisfies the condition expressed by the following expression (3).

$$(\cot \theta_1)^2 = [(c_1/c_2)^2 - 1] / [(\rho_2/\rho_1)^2 - (c_1/c_2)^2] \quad (3)$$

Therefore, if $\rho_1$ and $C_1$ of the propagation medium portion 6, and $\rho_2$ and $C_2$ of the fluid that fills the circumjacent space, are determined, then the incident angle $\theta_1$ is determined according to expression (3). Moreover, if the incident angle $\theta_1$ is determined, then the approach angle $\theta_2$ is also determined according to expression (2). If the incident angle $\theta_1$ and the approach angle $\theta_2$ are determined, then the inclination angle of the second surface region 8 of the propagation medium portion 6 can also be determined.

The above-mentioned fact is also applied to a case where the ultrasonic wave, which has propagated through the fluid that fills the circumjacent space, is received, and therefore, the ultrasonic wave arriving from a direction of the approach angle $\theta_2$ is selectively received.

In the first embodiment, by forming the propagation medium portion 6 of the aforementioned material, the acoustic velocity $C_1$ of the propagation medium portion 6 can be set to 180 m/s, and the density $\rho_1$ can be set to 200 kg/m$^3$. In a case where the circumjacent space is an ordinary space filled with air, the density $\rho_2$ of air is 1.22 kg/m$^3$ and the acoustic velocity $C_2$ is 340 m/s. Therefore, according to the relations of expression (2) and expression (3), it is proper to set the incident angle $\theta_1$ to 32° and set the approach angle $\theta_2$ to 89°. Since the approach angle $\theta_2$ is close to 90°, an ultrasonic wave transmitted in air travels almost parallel to the second surface region 8 that is a wave transmission surface. Therefore, a direction of transmitting and receiving an acoustic wave in the first embodiment is directed in a direction of arrow 90 of FIG. 1A along line segment B–B' in a plane that includes the second surface region 8 shown in FIG. 1A.

According to the first embodiment, almost no propagation loss occurs in the second surface region 8 that is the interface between the propagation medium portion 6 and the fluid that fills the circumjacent space, and therefore, it is not required to match their acoustic impedances at this interface with each other. Therefore, an ultrasonic wave emitted from inside the propagation medium portion 6 is refracted at the second surface region 8, that is the interface between the propagation medium portion 6 and the fluid that fills the circumjacent space, thereby allowing the ultrasonic wave to deflect in a direction along the plane that includes the second surface region 8. In addition, almost no propagation loss occurs in the second surface region 8, and therefore, a highly sensitive ultrasonic sensor that has high wave transmitting and receiving efficiency can be provided.

It is to be noted that the propagation medium portion 6 is not required to be constructed of a material whose density $\rho_1$ and acoustic velocity $C_1$ are uniform throughout an entire body, but is allowed to have a laminate structure in which a plurality of kinds of material layers having varied densities $\rho_1$ and acoustic velocities $C_1$ are laminated. When the laminate structure as described above is possessed, it is sometimes a case where an ultrasonic wave does not straightly travel through the propagation medium portion 6, which, however, poses no problem. An important point is that the density $\rho_1$ and the acoustic velocity $C_1$, and the incident angle $\theta_1$ of the propagation medium portion 6, are set so as to satisfy the aforementioned expressions in a region in the vicinity of the interface between the propagation medium portion 6 and fluid to be measured.

Operation of the ultrasonic transmitter-receiver of the first embodiment will be described next.

Figure 9A:
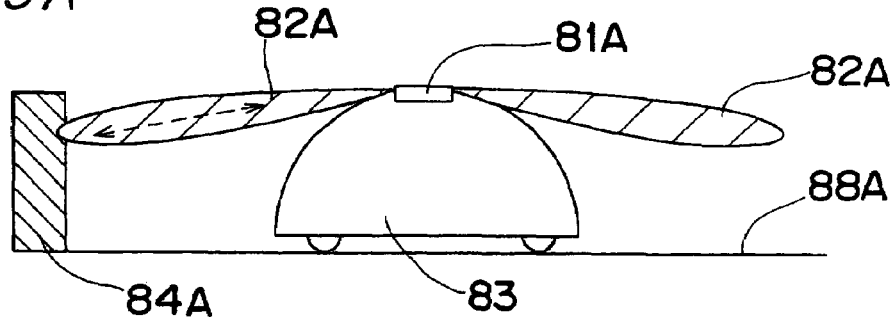
FIGS. 9A, 9B, and 9C are explanatory views when an ultrasonic transmitter-receiver according to a seventh embodiment of the present invention is applied to different fields.
Figure 9B:
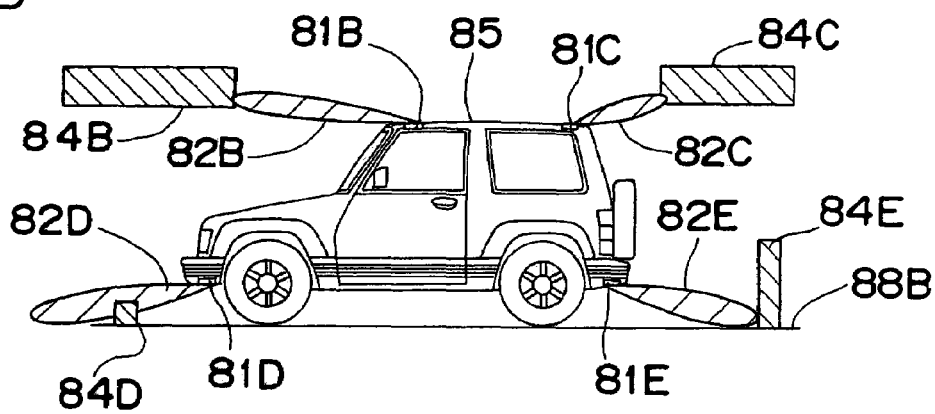
Figure 9C:
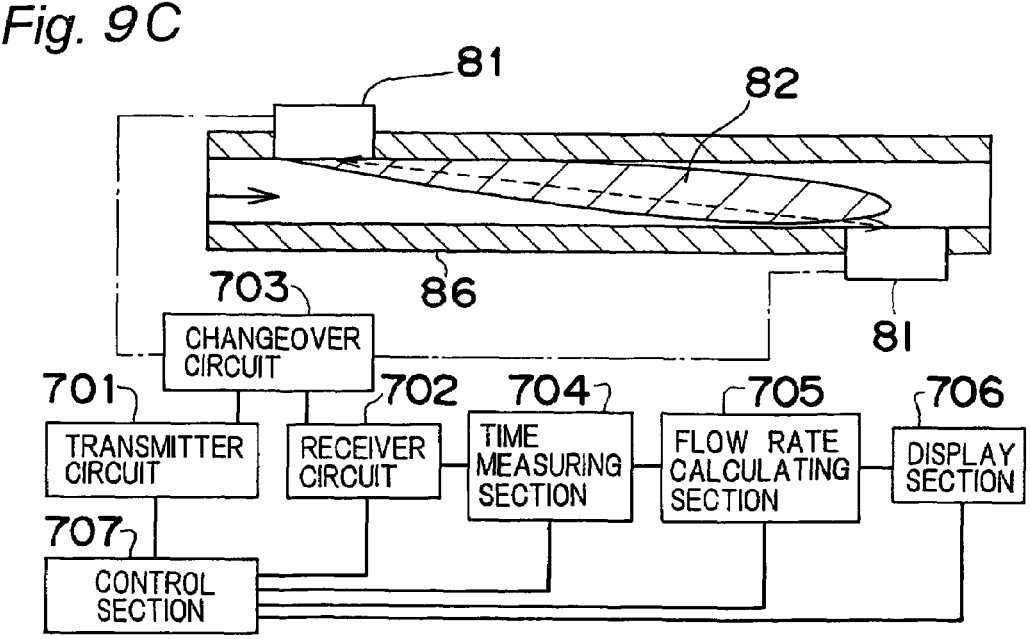
Figure 10:
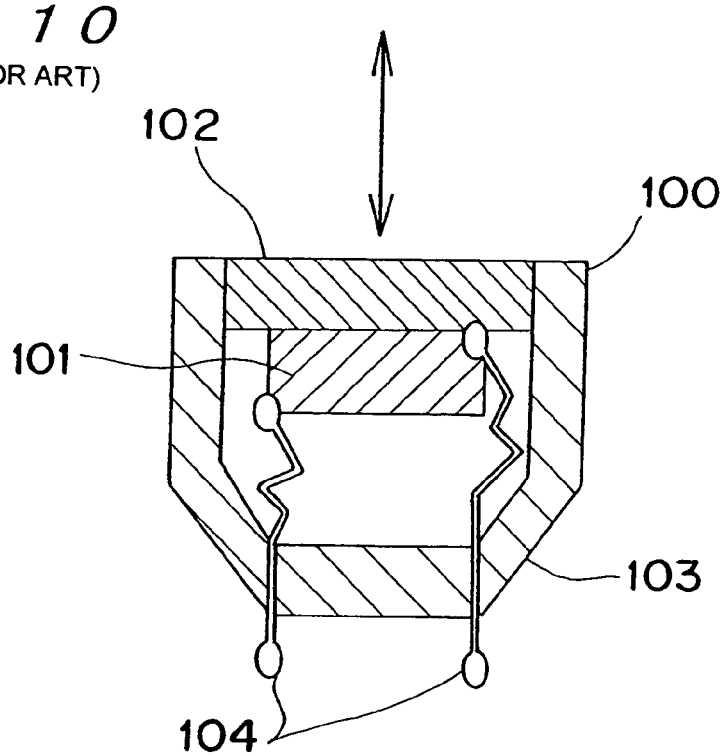
FIG. 10 is a sectional view of a conventional ultrasonic transmitter-receiver.
Figure 11:
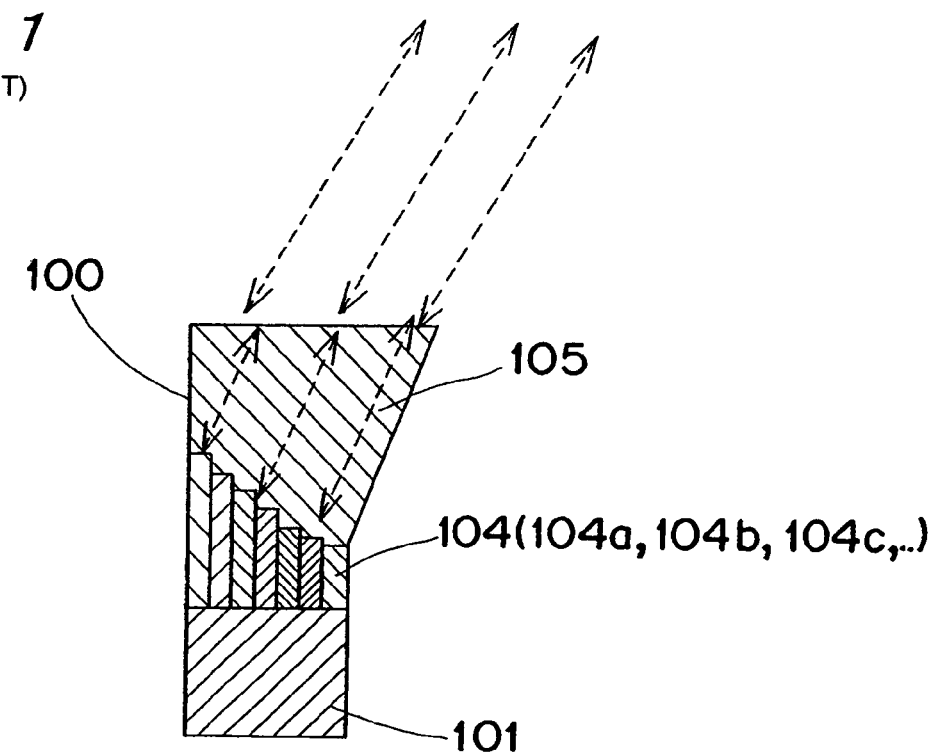
FIG. 11 is a sectional view of another conventional ultrasonic transmitter-receiver.

First of all, when transmitting a wave to the fluid that fills the circumjacent space, an ac voltage, a pulse voltage, or a burst voltage having a frequency in the vicinity of a resonance frequency (for example, about 100 kHz to 1 MHz) is applied from a transmitter circuit 701, that concurrently serves as a drive circuit shown in FIG. 9C, via the signal wires 5 to the ultrasonic transducer 2 (81 in FIG. 9C). By this operation, vibrations in the vicinity of the resonance frequency are excited in the ultrasonic transducer 2, and thus, the vibrations are radiated as an ultrasonic wave, on a condition of an efficiency of almost one, to the propagation medium portion 6 through the transducer casing 4 and the acoustic matching layer 3. An acoustic wave, which has propagated through the propagation medium portion 6, is refracted at the second surface region 8, that is the interface between the propagation medium portion 6 and the fluid that fills the circumjacent space, and radiated to the fluid that fills the circumjacent space in a state of an efficiency of almost one.

Next, when receiving the ultrasonic wave, which propagates through the fluid that fills the circumjacent space and reaches the ultrasonic transmitter-receiver 1, a path reverse to that of wave transmission holds with regard to the ultrasonic wave that has propagated from a wave transmission direction. The ultrasonic wave, which has entered the transmitter-receiver 1, reaches the ultrasonic transducer 2 on the condition of an efficiency of almost one and is converted into an electric signal and transmitted to an external electric circuit (for example, a receiver circuit 702) through the signal wires 5.

According to the first embodiment, there is provided the propagation medium portion 6 that exhibits the appropriate density $\rho_1$ and acoustic velocity $C_1$, and an ultrasonic wave is refracted at an appropriate angle. Therefore, propagation loss at an interface between these substances is made almost zero, thereby allowing a flow measurement to be achieved at a satisfactory signal-to-noise ratio. Then, according to the first embodiment, transmission and reception of an ultrasonic wave through a gas (for example, hydrogen gas or the like), which has had extreme difficulties in transmitting and receiving an ultrasonic wave in a conventional ultrasonic transmitter-receiver, becomes possible scarcely generating loss at the interface by appropriately refracting the ultrasonic wave by virtue of the propagation medium portion 6, and therefore, an application to flow measurement capable of measuring these gases becomes possible.

Furthermore, in the ultrasonic transmitter-receiver 1 of the first embodiment, an ultrasonic wave emitted from the propagation medium portion 6 is refracted at the second surface region 8, that is the interface between the propagation medium portion 6 and the fluid that fills the circumjacent space, and a direction in which the ultrasonic wave is transmitted and received is deflected in a direction along a plane that includes the second surface region 8. Therefore, in, for example, a flowmeter, projections and recesses concerning mounting of the transmitter-receiver in a measurement channel are removed, and a flowmeter free from disorder of fluid flow can be constructed. Moreover, the flowmeter can also be applied to an object detection in a horizontal direction and so on even when the flowmeter is mounted while being aligned with a horizontal plane of a variety of kinds of equipment that has a horizontal portion.

Second Embodiment

Figure 3A:
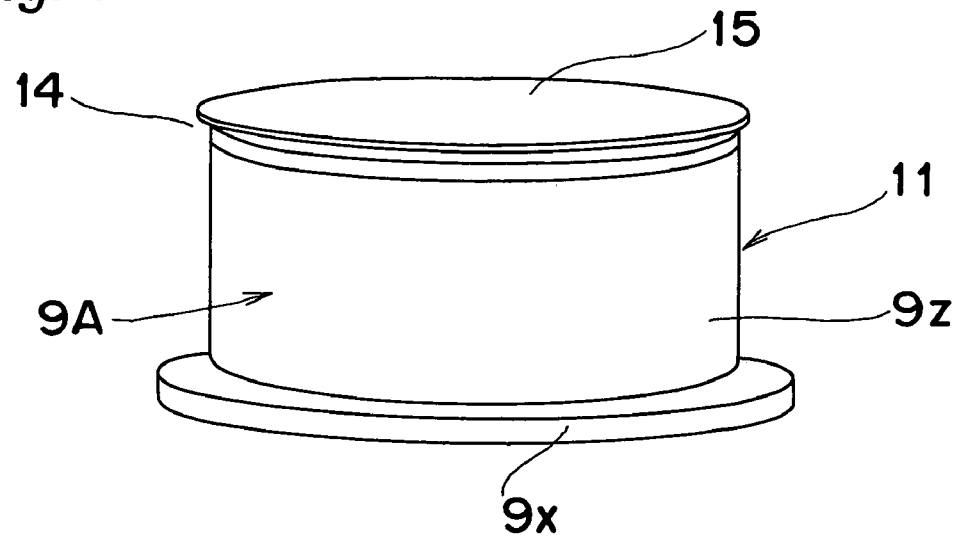
FIG. 3A is a perspective general view of an ultrasonic transmitter-receiver according to a second embodiment of the present invention.
Figure 3B:
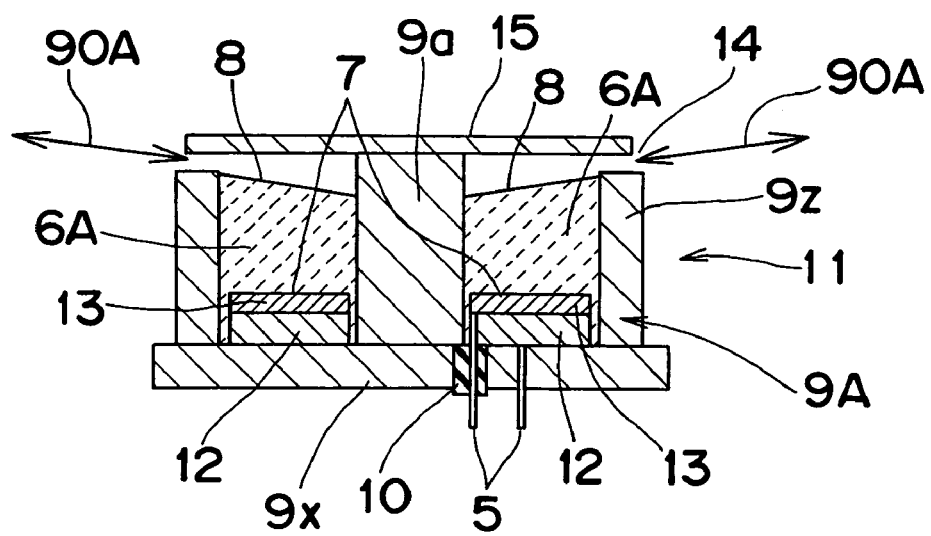
FIG. 3B is a sectional view along a cylinder center line of the ultrasonic transmitter-receiver of the second embodiment.
Figure 3C:
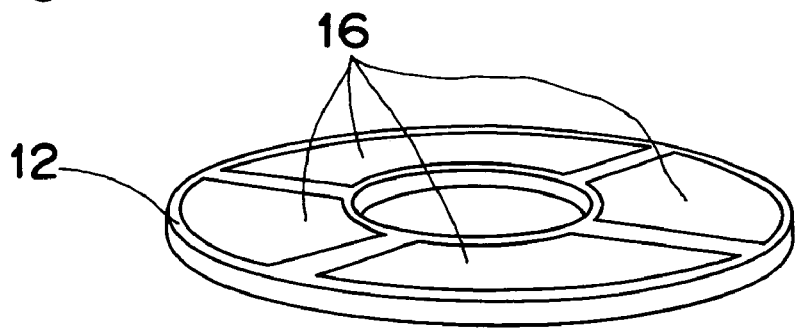
FIG. 3C is a perspective view showing one example of an electrode structure of an ultrasonic transducer of the ultrasonic transmitter-receiver of the second embodiment.

An ultrasonic transmitter-receiver as one example of the ultrasonic sensor according to a second embodiment of the present invention will be described with reference to FIGS. 3A, 3B and 3C. FIG. 3A is a perspective view of an appearance of an ultrasonic transmitter-receiver 11 of the second embodiment. FIG. 3B is a sectional view including a central axis of cylindrical ultrasonic transmitter-receiver 11. FIG. 3C is a perspective view showing one example of an electrode structure of an ultrasonic transducer 12. Like reference numerals are given to common members of the second embodiment and the first embodiment. A propagation medium portion 6A corresponds to the propagation medium portion 6 of the first embodiment, and a housing 9A corresponds to the housing 9 of the first embodiment.

Hereinafter, characteristic points of the ultrasonic transmitter-receiver 11 of the second embodiment will be described below, and no description is provided for portions similar to those of the ultrasonic transmitter-receiver 1 of the first embodiment and the aforementioned corresponding portions.

In the ultrasonic transmitter-receiver 11 of the second embodiment, a cylindrical side portion 9z is fixed to a disk-shaped terminal plate 9x constituting the housing 9A, thereby providing a construction symmetrical to an axis around central shaft 9a fixed to a center of the terminal plate 9x. Therefore, an ultrasonic transducer 12 and an acoustic matching layer 13 arranged on the disk-shaped terminal plate 9x of the housing 9A are constructed in a ring-like shape. Moreover, a disk-shaped protecting section 15, which is part of the housing 9A and of which a central portion is connected to the central shaft 9a, is further provided to protect second surface region 8. A ring-shaped opening 14 is provided between the housing 9A and the protecting section 15, and an ultrasonic wave is transmitted and received in a direction of arrow 90A through the opening 14. A space, which is located inside the housing 9A and is other than ultrasonic transducer 12 and acoustic matching layer 13, is almost filled with the propagation medium portion 6A. Then, the propagation medium portion 6A has a first surface region 7 that faces the acoustic matching layer 13 and the ultrasonic transducer 12 (note that the first surface region 7 directly faces the acoustic matching layer 13) and a second surface region 8 that faces the fluid that fills the circumjacent space. Further, the second surface region 8 of the propagation medium portion 6A is approximately uniformly inclined at a prescribed angle from a periphery toward a central side with respect to the central shaft 9a so that the second surface region 8 does not become parallel to the first surface region 7.

In the second embodiment, concrete transmission and reception of an ultrasonic wave are performed with high efficiency similarly to the first embodiment, so that effects similar to those of the first embodiment can be produced. A difference from the first embodiment resides in that omnidirectional wave transmission and reception around the central shaft 9a can be achieved since the ultrasonic transmitter-receiver 11 has a structure symmetrical to the central shaft 9a. When the circumjacent space is filled with a gas, wave transmission and reception become almost horizontal, and an application to omnidirectional object sensing becomes possible.

FIG. 3C shows one example of the electrode structure of the ultrasonic transducer 12, and reference numeral 16 denotes segmented electrode sections constructed on a surface of an electrode. By the electrode sections 16 segmented as shown in FIG. 3C, a vibration generating section can be controlled. Therefore, scanning by an ultrasonic wave in a circumferential direction becomes possible, and an application to object sensing and so on with the direction specified becomes possible.

This segmentation of the electrode sections is allowed to be achieved on at least one surface of the electrode sections 16 formed on front and rear sides. Moreover, a similar effect can be obtained also by arranging the ultrasonic transducer 12 while segmenting the transducer 12 itself. Although a number of segmentation of the electrode section 6 is four in FIG. 3C, the number of segmentations is arbitrary, and it is not necessarily required to provide an identical shape or a symmetrical shape.

Third Embodiment

Figure 4A:
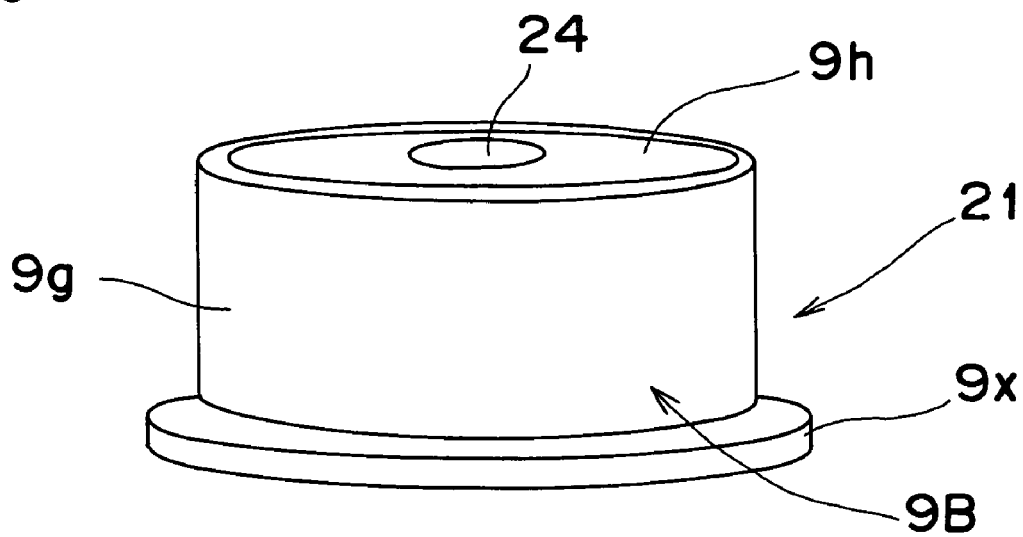
FIG. 4A is a perspective general view of one ultrasonic transmitter-receiver according to a third embodiment of the present invention.
Figure 4B:
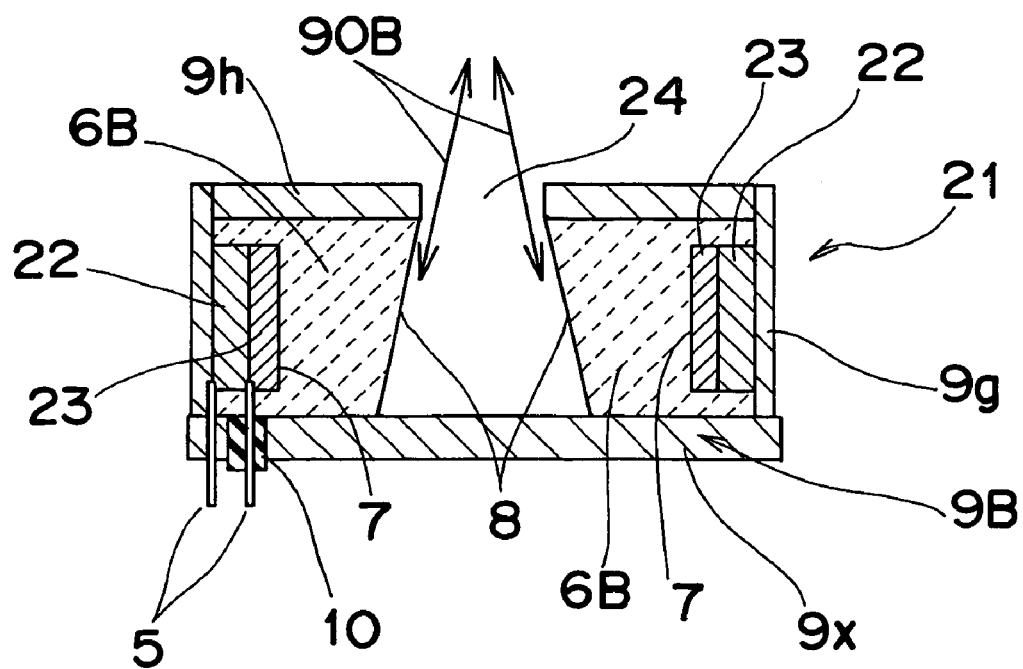
FIG. 4B is a sectional view along a cylinder center line of the ultrasonic transmitter-receiver of FIG. 4A of the third embodiment.
Figure 5A:
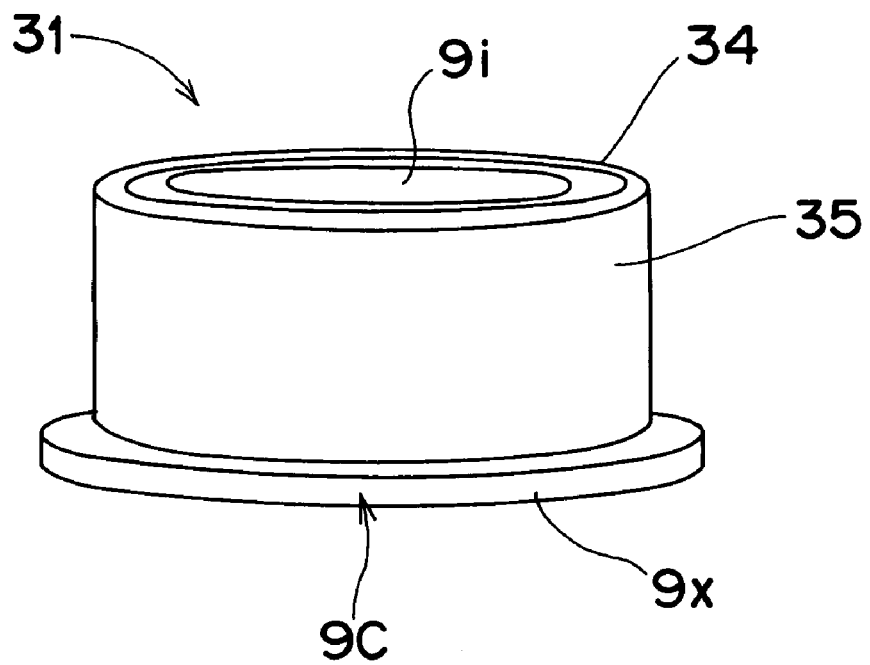
FIG. 5A is a perspective general view of another ultrasonic transmitter-receiver of the third embodiment of the present invention.
Figure 5B:
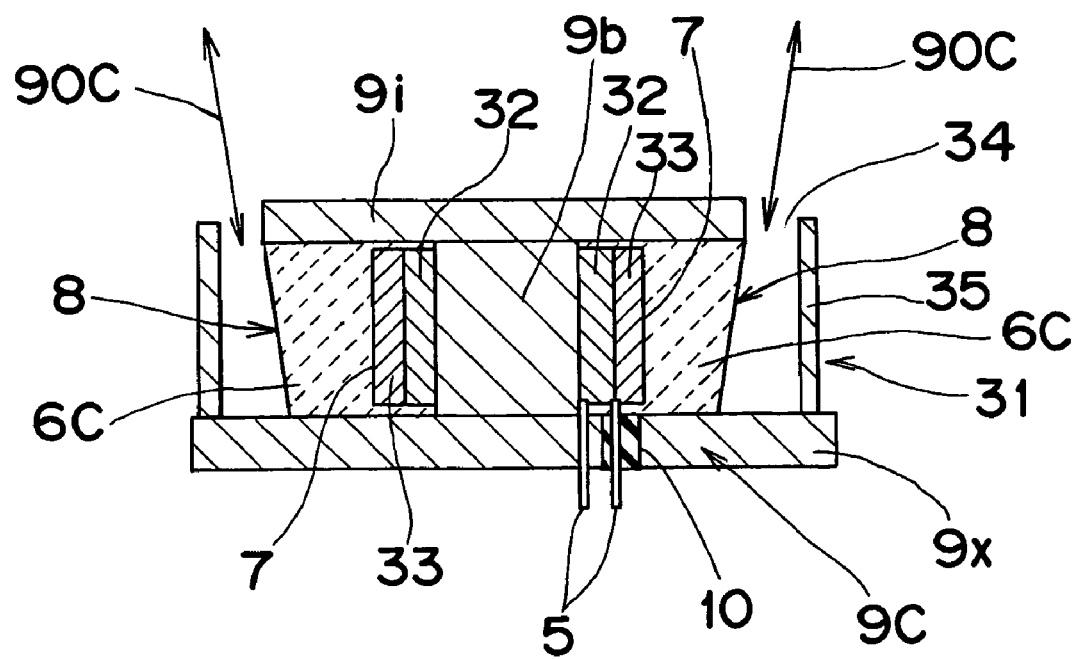
FIG. 5B is a sectional view along a cylinder center line of the ultrasonic transmitter-receiver of FIG. 5A of the third embodiment.

An ultrasonic transmitter-receiver as one example of the ultrasonic sensor according to a third embodiment of the present invention will be described with reference to FIGS. 4A and 4B and FIGS. 5A and 5B. FIG. 4A shows a perspective view of an external appearance of an ultrasonic transmitter-receiver 21 of the third embodiment. FIG. 4B shows a cross section of the cylindrical ultrasonic transmitter-receiver 21 including its central axis. FIG. 5A shows a perspective view of an external appearance of another ultrasonic transmitter-receiver 31 of the third embodiment. FIG. 5B shows a cross section of cylindrical ultrasonic transmitter-receiver 31 including its central shaft 9b. Like reference numerals are given to common members of the third embodiment and the aforementioned first and second embodiments. It is to be noted that propagation medium portions 6B and 6C correspond to the propagation medium portion 6 or 6A of the foregoing embodiments, and housings 9B and 9C correspond to the housing 9 or 9A of the foregoing embodiments.

Hereinafter, characteristic points of the ultrasonic transmitter-receiver 21 and the ultrasonic transmitter-receiver 31 of the third embodiment will be described below, and no description is provided for portions similar to those of the ultrasonic transmitter-receiver 1 of the first embodiment and the ultrasonic transmitter-receiver 11 of the second embodiment and the aforementioned corresponding portions.

In the housing 9B of the ultrasonic transmitter-receiver 21 of the third embodiment, as shown in FIGS. 4A and 4B, a terminal plate 9x is fixed to a lower end of a cylindrical side portion 9g, and a disk-shaped upper plate 9h having a circular opening 24 in a central portion is fixed to an upper end of the side portion 9g, so that the housing 9B is constructed symmetrically relative to an axis around an imaginary central axis. An ultrasonic transducer 22 and an acoustic matching layer 23 fixed to an inner surface of the side portion 9g of the housing 9B are cylindrically constructed. Moreover, the propagation medium portion 6B is housed and arranged in the housing 9B so that the propagation medium portion 6B does not protrude inwardly of the central opening 24 of the disk-shaped upper plate 9h of the housing 9B to protect the second surface region 8 by an entire body of the housing 9B, and transmission and reception of an ultrasonic wave are performed in a direction of arrow 90B through the central opening 24 of the upper plate 9h of the housing 9B. That is, a space, which is located inside the housing 9B and is other than the ultrasonic transducer 22, the acoustic matching layer 23 and a central portion, is filled with the propagation medium portion 6B. Then, the propagation medium portion 6B has a first surface region 7 that faces the acoustic matching layer 23 and the ultrasonic transducer 22 (note that the first surface region 7 directly faces the acoustic matching layer 23) and a second surface region 8 that faces the fluid that fills the circumjacent space (the second surface region 8 faces the space in the central portion in FIG. 4B). Further, the second surface region 8 of the propagation medium portion 6B is inclined at a prescribed angle forming a conical surface so that the second surface region 8 expands from an upper end to a lower end roughly uniformly with respect to the central axis and does not become parallel to the first surface region 7.

On the other hand, as shown in FIGS. 5A and 5B, in the housing 9C of another ultrasonic transmitter-receiver 31 of the third embodiment, a terminal plate 9x is fixed to a lower end of a cylindrical side portion 35, and a central portion of a disk-shaped upper plate 9i is fixed to a central shaft 9b fixed to a central portion of the terminal plate 9x, so that the housing 9C is constructed symmetrically relative to an axis around the central shaft 9b. An ultrasonic transducer 32 and an acoustic matching layer 33 fixed around the central shaft 9b are cylindrically constructed. Moreover, a propagation medium portion 6C is housed and arranged in the housing 9C so that the propagation medium portion 6C does not protrude outwardly of a periphery of the upper plate 9i of the housing 9C to protect the second surface region 8 by a protecting portion 35 that is the cylindrical side portion fixed to the terminal plate 9x of the housing 9C. A ring-shaped opening 34 is provided between the housing 9C and the protecting portion 35, and transmission and reception of an ultrasonic wave are performed in a direction of arrow 90C through the opening 34. That is, a space, which is located inside the housing 9C and is other than the ultrasonic transducer 32, the acoustic matching layer 33, and the peripheral portion, is filled with the propagation medium portion 6C. Then, the propagation medium portion 6C has a first surface region 7 that faces the acoustic matching layer 33 and the ultrasonic transducer 32 (note that the first surface region 7 directly faces the acoustic matching layer 33), and a second surface region 8 that faces the fluid that fills the circumjacent space (the second surface region 8 faces the space in the peripheral portion in FIG. 5B). Further, the second surface region 8 of the propagation medium portion 6C is inclined at a prescribed angle forming a conical surface so that the second surface region 8 expands from the lower end to the upper end roughly uniformly with respect to the central axis and does not become parallel to the first surface region 7.

In the third embodiment, the concrete transmission and reception of an ultrasonic wave are performed with high efficiency similarly to the first embodiment and the second embodiment, and effects similar to those of the first embodiment and the second embodiment can be produced. A difference from the second embodiment resides in that the transmission and reception of an ultrasonic wave are performed in a forward direction (upward direction in FIGS. 4B and 5B) of the ultrasonic transmitter-receivers 21 and 31, and an application to generally materialized ultrasonic transmitter-receivers is possible.

Fourth Embodiment

Figure 6A:
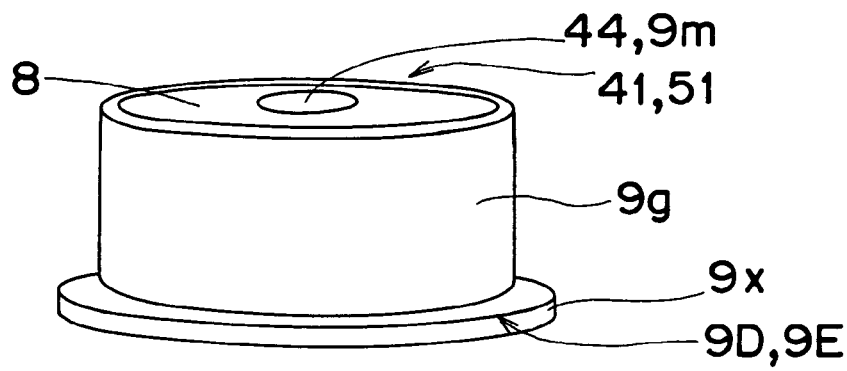
FIG. 6A is a perspective general view of an ultrasonic transmitter-receiver according to a fourth embodiment of the present invention.
Figure 6B:
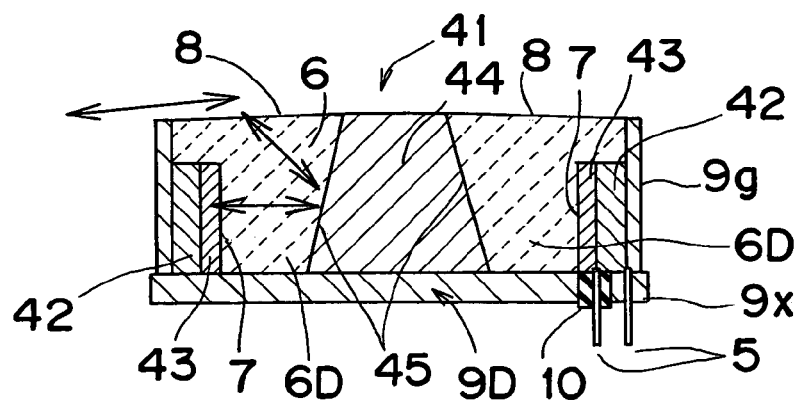
FIG. 6B is a sectional view along a cylinder center line of the ultrasonic transmitter-receiver of the fourth embodiment.
Figure 6C:
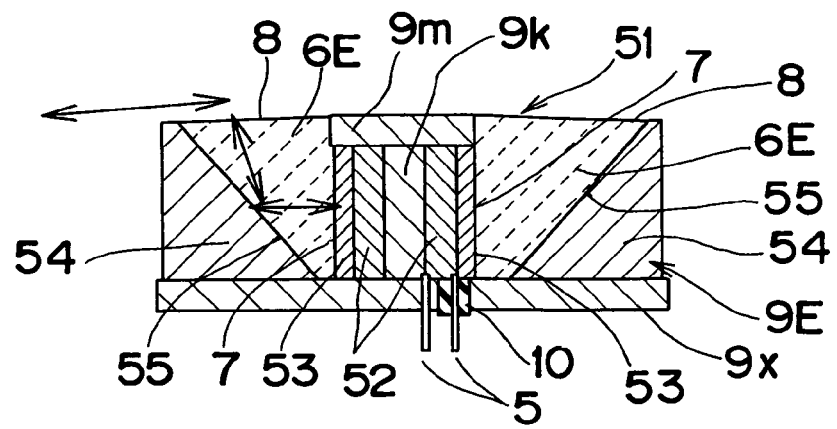
FIG. 6C is a sectional view including a central axis of another cylindrical ultrasonic transmitter-receiver of the fourth embodiment.
Figure 6D:
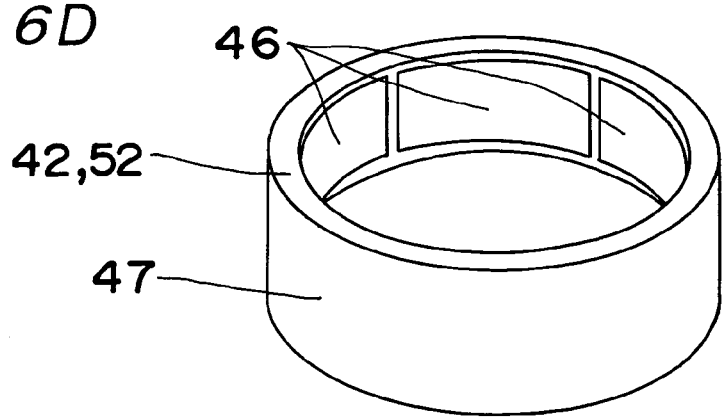
FIG. 6D is a perspective view showing one example of an electrode surface of the ultrasonic transducer of the ultrasonic transmitter-receiver of the fourth embodiment.

An ultrasonic transmitter-receiver as one example of the ultrasonic sensor according to a fourth embodiment of the present invention will be described with reference to FIGS. 6A, 6B, 6C and 6D. FIG. 6A shows a perspective view of an external appearance of an ultrasonic transmitter-receiver 41 and an ultrasonic transmitter-receiver 51 of the fourth embodiment. FIG. 6B is a sectional view of cylindrical ultrasonic transmitter-receiver 41 including its central shaft. FIG. 6C is a sectional view of another cylindrical ultrasonic transmitter-receiver 51 of the fourth embodiment including its central shaft. FIG. 6D shows a perspective view of one example of electrode surfaces of ultrasonic transducers 42 and 52 of the ultrasonic transmitter-receiver of the fourth embodiment. Like reference numerals are given to common members of the fourth embodiment and the first through third embodiments. It is to be noted that propagation medium portions 6D and 6E correspond to the propagation medium portion 6, 6A or the like of the foregoing embodiments. Housings 9D and 9E correspond to the housing 9, 9A or the like of the foregoing embodiments.

Hereinafter, characteristic points of the ultrasonic transmitter-receiver 41 and the ultrasonic transmitter-receiver 51 of the fourth embodiment will be described below, and no description is provided for portions similar to those of the ultrasonic transmitter-receiver 1 of the first embodiment and the ultrasonic transmitter-receivers 11 and 21 of the second embodiment and the aforementioned corresponding portions.

In the housing 9D of the ultrasonic transmitter-receiver 41 of the fourth embodiment, as shown in FIGS. 6A and 6B, a terminal plate 9x is fixed to a lower end of a cylindrical side portion 9g, and a truncated-circular-cone-shaped reflector 44 is fixed to a central portion of the terminal plate 9x, so that the housing 9D is constructed symmetrically relative to an axis around a central axis of the reflector 44. An ultrasonic transducer 42 and an acoustic matching layer 43 fixed to the side portion 9g of the housing 9D and an inner surface of the terminal plate 9x are cylindrical, and the acoustic matching layer 43 is arranged inside the ultrasonic transducer 42. Moreover, the propagation medium portion 6D is housed and arranged in the housing 9D so that the propagation medium portion 6D does not protrude from an upper end surface of the reflector 44 of the housing 9D and an upper end surface of the side portion 9g. Then, the propagation medium portion 6D has a first surface region 7 parallel to a vibration surface of the ultrasonic transducer 42, and a second surface region 8 brought into contact with a fluid that fills the circumjacent space and is brought into contact with the reflector 44 provided adjacent to the propagation medium portion 6D by a third surface region 45.

The reflector 44 is constructed of a metallic material of stainless steel or the like, and, when the propagation medium portion 6 is formed of a nanoporous dry gel that has a main ingredient of, for example, silica, a reflection efficiency in the third surface region 45 becomes almost one. With regard to the reflector 44, an inclination angle is set with respect to the first surface region 7 and the second surface region 8 so that an incident angle of an ultrasonic wave relative to the second surface region 8 satisfies expression (3).

The ultrasonic transducer 42 is excited with vibrations in the vicinity of a resonance frequency, and the vibrations are radiated as an ultrasonic wave on the condition of an efficiency of almost one roughly on a central side of the propagation medium portion 6D through the acoustic matching layer 43. The acoustic wave, which has propagated through the propagation medium portion 6D, is reflected on the third surface region 45 that forms an interface with the reflector 44, with an efficiency of almost one to propagate with a direction thereof changed roughly toward the second surface region 8 side, then refracted at the second surface region 8 that is an interface between the propagation medium portion 6D and the fluid that fills the circumjacent space, and radiated to the fluid that fills the circumjacent space with an efficiency of almost one.

Moreover, when receiving the ultrasonic wave, which propagates through the fluid that fills the circumjacent space and reaches the ultrasonic transmitter-receiver 41, a path reverse to that of wave transmission holds with regard to the ultrasonic wave that has propagated from a direction of wave transmission. The ultrasonic wave, which enters the second surface region 8 of the ultrasonic transmitter-receiver 41 with an efficiency of almost one, propagates through the propagation medium portion 6D and is reflected with an efficiency of almost one on the third surface region 45, that forms the interface with the reflector 44, to propagate with a direction thereof changed roughly toward the ultrasonic transducer 42 side and reaches the ultrasonic transducer 42, and then converted into electric signals by the ultrasonic transducer 42.

With the above construction, the ultrasonic transmitter-receiver 41 also becomes able to highly efficiently transmit and receive an ultrasonic wave to and from the fluid that fills the circumjacent space, and effects similar to those of the first embodiment can be produced.

On the other hand, as shown in FIGS. 6A and 6C, in the housing 9E of another ultrasonic transmitter-receiver 51 of the fourth embodiment, a terminal plate 9x is fixed to a lower end of a sectionally triangular cylindrical reflector 54, a columnar central shaft 9k is fixed to a central portion of the terminal plate 9x, and a disk-shaped upper plate 9m is fixed like a protruded flange to an upper end of the central shaft 9k, so that the housing 9E is constructed symmetrically relative to an axis around a central axis of the reflector 54. An ultrasonic transducer 52 and an acoustic matching layer 53 fixed to the central shaft 9k of the housing 9E and inner surfaces of upper plate 9m and the terminal plate 9x are cylindrical, and the acoustic matching layer 53 is arranged outside the ultrasonic transducer 52. Moreover, propagation medium portion 6E is housed and arranged in the housing 9E so that the propagation medium portion 6E does not protrude above an upper end surface of the reflector 54 of the housing 9E and an upper end surface of the upper plate 9m. Then, the propagation medium portion 6E has a first surface region 7 parallel to a vibration surface of the ultrasonic transducer 52 and a second surface region 8 brought into contact with fluid that fills a circumjacent space, and is brought into contact with the reflector 54 provided adjacent to the propagation medium portion 6E by a third surface region 55. The reflector 54 has a material and an inclination angle similar to those of the reflector 44.

The ultrasonic transducer 52 is excited with vibrations in the vicinity of a resonance frequency, and the vibrations are radiated as an ultrasonic wave roughly to a peripheral side of the propagation medium portion 6E through the acoustic matching layer 53 on the condition of an efficiency of almost one. The ultrasonic wave, which has propagated through the propagation medium portion 6E, is reflected on the third surface region 55, that forms an interface with the reflector 54, with an efficiency of almost one to propagate with a direction thereof changed roughly toward the second surface region 8 side, refracted at the second surface region 8 that is an interface between the propagation medium portion 6E and the fluid that fills the circumjacent space, and then radiated to the fluid that fills the circumjacent space with an efficiency of almost one.

Moreover, when receiving the ultrasonic wave, which propagates through the fluid that fills the circumjacent space and reaches the ultrasonic transmitter-receiver 51, a path reverse to that of wave transmission holds with regard to the ultrasonic wave that has propagated from a wave transmission direction. The ultrasonic wave, which enters the second surface region 8 of the ultrasonic transmitter-receiver 51 with an efficiency of almost one, propagates through the propagation medium portion 6E and is reflected at the third surface region 55, that forms the interface with the reflector 54, with an efficiency of almost one to propagate with a direction thereof changed roughly toward the ultrasonic transducer 52 side and reach the ultrasonic transducer 52, and then converted into electric signals by the ultrasonic transducer 52.

With the above construction, the ultrasonic transmitter-receiver 51 also becomes able to highly efficiently transmit and receive an ultrasonic wave to and from the fluid that fills the circumjacent space, and effects similar to those of the first embodiment can be produced.

It is to be noted that a plurality of reflectors 44 and 54 of the fourth embodiment may be arranged, and in this case, there exists a plurality of third surface regions 45 and 55 in terms of construction. Moreover, in this case, a construction in which the first surface region 7 and the second surface region 8 are parallel to each other also holds, and at least one of the plurality of third surface regions 45 and 55 is required to be inclined at a prescribed angle with respect to the second surface region 8.

The ultrasonic transmitter-receiver 41 and the ultrasonic transmitter-receiver 51 have a structure in which wave transmission and reception can be performed omnidirectionally around the central axis similarly to the second embodiment. When the circumjacent space is filled with a gas, wave transmission and reception become almost horizontal, and an application to omnidirectional object sensing and the like becomes possible.

Moreover, FIG. 6D shows one example of an electrode structure of the ultrasonic transducers 42 and 52. Reference numeral 46 denotes segmented electrodes constructed on inner side surfaces of the cylindrical ultrasonic transducers 42 and 52, and reference numeral 47 denotes a common electrode constructed on an outer side surface. By electrode sections 46 segmented as shown in FIG. 6D, a vibration generating section can be controlled. Therefore, scanning by an ultrasonic wave in a circumferential direction becomes possible, and an application to object sensing and the like with the direction specified becomes possible.

As shown in FIG. 6D, segmentation of the electrode sections 46 is allowed to be achieved on at least one side surface of the electrode sections formed on the inner and outer side surfaces. Moreover, a similar effect can be obtained also by arranging the ultrasonic transducers 42 and 52 while segmenting the transducers 42 and 52 themselves. A number of segments of the electrode is arbitrary, and it is not necessarily required to provide an identical shape or a symmetrical shape.

Fifth Embodiment

Figure 7:
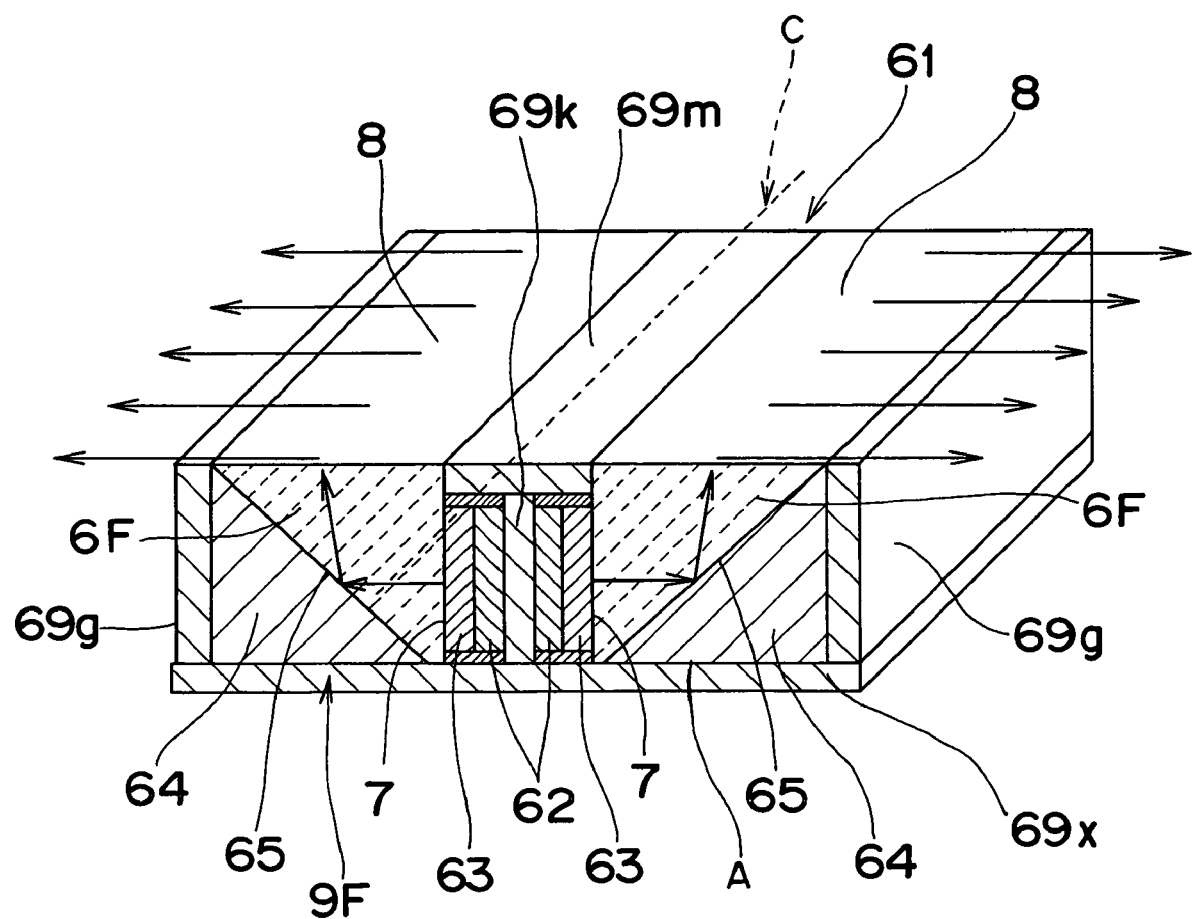
FIG. 7 is a partially sectional perspective view of an ultrasonic transmitter-receiver according to a fifth embodiment of the present invention.

The ultrasonic transmitter-receiver as one example of the ultrasonic sensor according to a fifth embodiment of the present invention will be described with reference to FIG. 7. FIG. 7 is a perspective view of an external appearance of an ultrasonic transmitter-receiver 61 of the fifth embodiment, also serving as a sectional view for explaining an internal structure with regard to plane A on this side of FIG. 7, the plane is actually covered with a housing side portion. Moreover, like reference numerals are given to common members of the fifth embodiment and the first through fourth embodiments. It is to be noted that propagation medium portions 6F correspond to the propagation medium portions 6, 6A or the like of the first embodiment, and a housing 9F corresponds to the housing 9, 9A or the like of the first embodiment.

Hereinafter, characteristic points of the ultrasonic transmitter-receiver 61 of the fifth embodiment will be described below, and no description is provided for portions similar to those of the ultrasonic transmitter-receiver 1 of the first embodiment, the ultrasonic transmitter-receivers 11 and 21 of the second embodiment, the ultrasonic transmitter-receiver 31 of the third embodiment, the ultrasonic transmitter-receivers 41 and 51 of the fourth embodiment and the aforementioned corresponding portions.

In the ultrasonic transmitter-receiver 61 of the fifth embodiment, a portion, which correspond to the cylindrical or conical portion of the ultrasonic transmitter-receivers 41 and 51 of the fourth embodiment, are made rectangular. A rectangular plate-shaped terminal plate 69x is fixed to a lower end of a rectangular plate-shaped side portion 69g, a triangular prismatic reflector 64 is fixed to peripheral portions of the side portion 69g and the terminal plate 69x, and a rectangular disk-shaped upper plate 69m is fixed, while protruded like a flange, to an upper end of a rectangular plate-shaped central shaft 69k, thereby providing a symmetrical construction with respect to a center line C. Ultrasonic transducers 62 and acoustic matching layers 63 are rectangular plates and are fixed to an inner surface of the central shaft 69k, and the acoustic matching layers 63 are arranged outside the ultrasonic transducers 62. The propagation medium portions 6F have a first surface region 7 parallel to a vibration surface of a corresponding ultrasonic transducer 62, and a second surface region 8 brought into contact with fluid that fills a circumjacent space, and is brought into contact with reflectors 64 provided adjacent to the propagation medium portions 6F by third surface regions 65. The reflectors 64 have a material and an inclination angle which are similar to those of the reflector 44.

The fifth embodiment differs from the fourth embodiment in that transmission and reception of an ultrasonic wave in the ultrasonic transmitter-receiver 61 of the fifth embodiment are performed transversely in FIG. 7 and symmetrically with respect to the center line C. Even in this case, ultrasonic waves are radiated to the propagation medium portions 6F through respective acoustic matching layers 63 on the condition of an efficiency of almost one, and the ultrasonic waves, which have propagated through the propagation medium portion 6F, are reflected at the third surface region 65, that forms an interface with reflector 64, with an efficiency of almost one to change a direction roughly toward the second surface region 8 side. Further, the ultrasonic waves are refracted at the second surface regions 8 that are interfaces between the propagation medium portions 6F and the fluid that fills the circumjacent spaces and radiated to the fluid that fills the circumjacent space, with an efficiency of almost one. Moreover, a path reverse to that of wave transmission holds with regard to an ultrasonic wave that has propagated from a direction of wave transmission. The ultrasonic waves, which have entered the second surface regions 8 of the ultrasonic transmitter-receiver 61 with an efficiency of almost one, propagate through the propagation medium portions 6F and are reflected at the third surface regions 65, that form the interfaces with reflectors 64, with an efficiency of almost one to reach the ultrasonic transducers 62, and then converted into electric signals by the ultrasonic transducers 62.

With the above construction, the ultrasonic transmitter-receiver 61 also becomes able to highly efficiently transmit and receive ultrasonic waves to and from the fluid that fills the circumjacent space, and effects similar to those of the first embodiment can be produced. Moreover, the ultrasonic transmitter-receiver 61 has a structure such that wave transmission and reception in a transverse direction can be performed, and when the circumjacent space is filled with a gas, transmission and reception waves become almost horizontal, and an application to transverse object sensing and the like becomes possible.

Sixth Embodiment

Figure 8A:
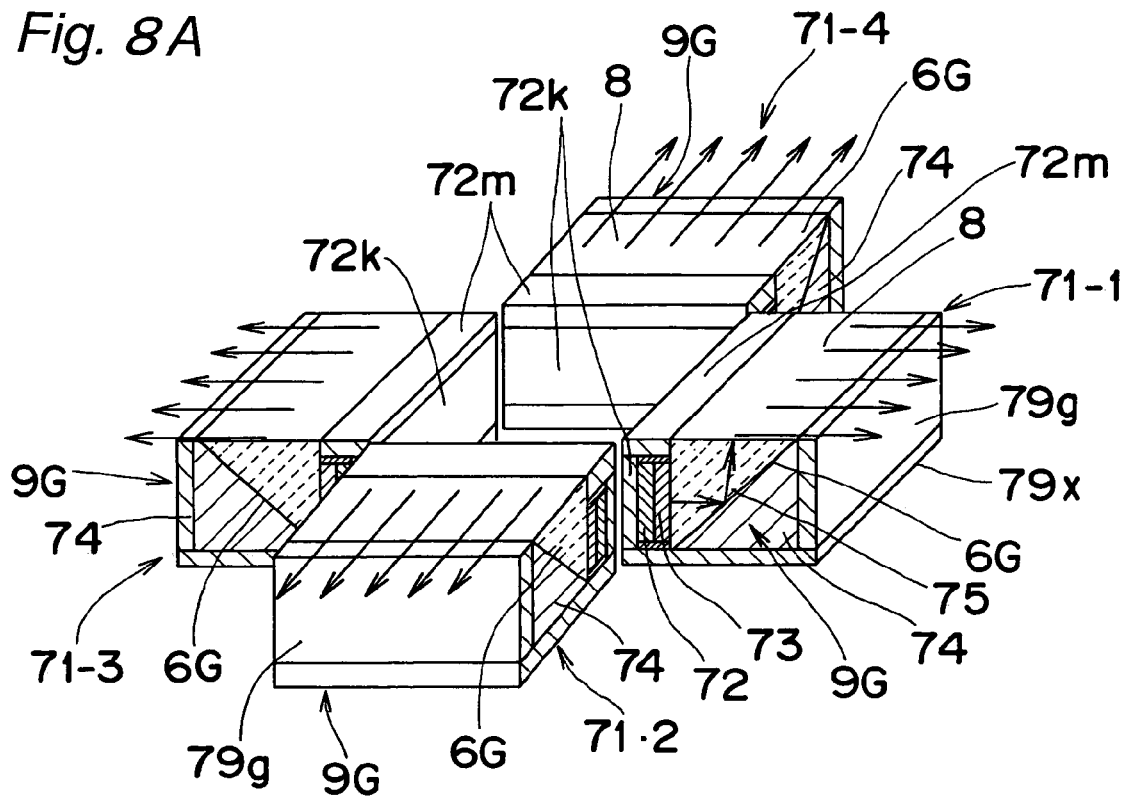
FIGS. 8A and 8B are general views of an ultrasonic transmitter-receiver according to a sixth embodiment of the present invention.
Figure 8B:
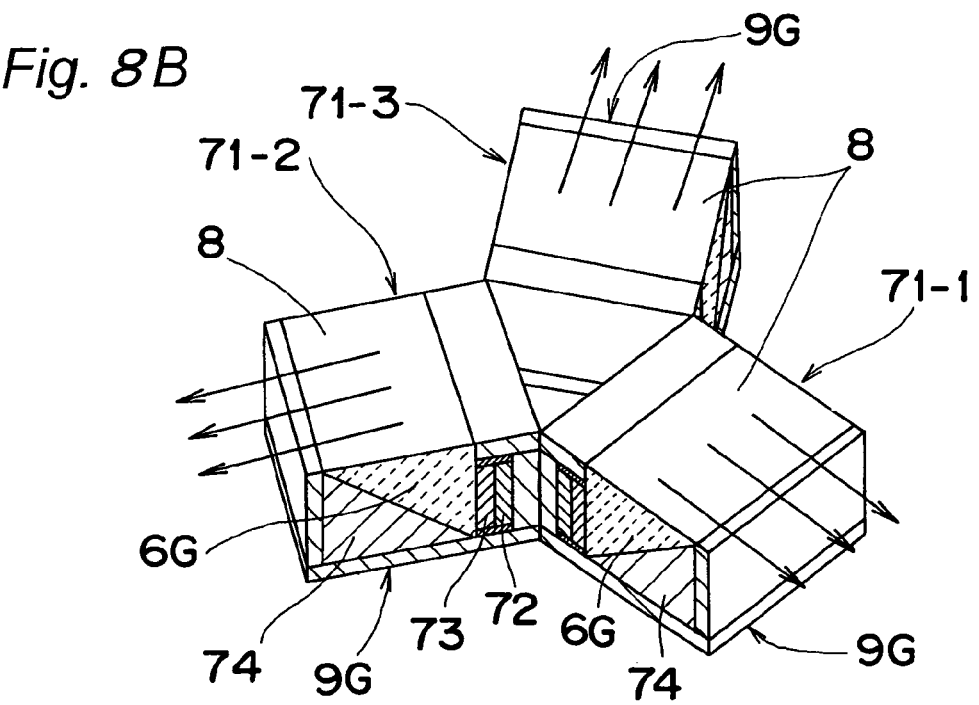

An ultrasonic transmitter-receiver as one example of the ultrasonic sensor according to a sixth embodiment of the present invention will be described with reference to FIGS. 8A and 8B. FIGS. 8A and 8B are perspective views of a plurality of arranged ultrasonic transmitter-receivers 71-1, 71-2, 71-3 and 71-4 of the sixth embodiment, and like reference numerals are given to common members of the sixth embodiment and the first through fifth embodiments. It is to be noted that a propagation medium portion 6G corresponds to the propagation medium portion 6 of the first embodiment, the propagation medium portions 6F of the fifth embodiment and so on, and a housing 9G corresponds to the housing 9 of the first embodiment, the housing 9F of the fifth embodiment and so on. A central shaft 79k corresponds to the central plate 69k of the fifth embodiment, and a side portion 79g corresponds to the side portions 69g of the fifth embodiment. A terminal plate 79x corresponds to the terminal plate 69x of the fifth embodiment, a reflector 74 corresponds to the reflectors 64 of the fifth embodiment, and an upper plate 79m corresponds to the upper plates 69m of the fifth embodiment.

Hereinafter, characteristic points of the ultrasonic transmitter-receivers 71-1, 71-2, 71-3 and 71-4 of the sixth embodiment will be described below, and no description is provided for portions similar to those of other embodiments and the aforementioned corresponding portions.

The ultrasonic transmitter-receivers 71-1, 71-2, 71-3 and 71-4 of the sixth embodiment have a structure in which the ultrasonic transmitter-receiver 61 of the fifth embodiment is divided along center line C. Therefore, although transmission and reception of an ultrasonic wave are limited to one direction, the transmission and reception of an ultrasonic wave are performed with high efficiency similarly to the fifth embodiment, and effects similar to those of the first embodiment can be produced. When a circumjacent space is filled with a gas, the wave transmission and reception becomes almost horizontal, and an application to object sensing and the like becomes possible.

FIG. 8A shows a construction in which the four ultrasonic transmitter-receivers 71-1, 71-2, 71-3 and 71-4 are employed to allow ultrasonic waves to be transmitted and received in depthwise and transverse directions, and FIG. 8B shows a construction in which three ultrasonic transmitter-receivers 71-1, 71-2 and 71-3 are employed to allow ultrasonic waves to be transmitted and received in three directions at intervals of 120 degrees. As shown in FIGS. 8A and 8B, by arranging an arbitrary plural number of ultrasonic transmitter-receivers 71 in arbitrary directions, control of directivity corresponding to an application becomes possible, and a range of applications can be widened.

Seventh Embodiment

Application equipment of an ultrasonic transmitter-receiver as one example of the ultrasonic sensor according to the seventh embodiment of the present invention will be described with reference to FIGS. 9A, 9B and 9C. FIG. 9A shows an obstacle detection system of a self-propelled type robot such as a cleaning robot. FIG. 9B shows a peripheral obstacle detection system of an automobile. FIG. 9C shows an application to an ultrasonic flowmeter.

In FIGS. 9A, 9B and 9C, reference numerals 81, 81A, 81B, 81C, 81D and 81E show ultrasonic transmitter-receivers capable of performing transmission and reception of an ultrasonic wave almost in a horizontal direction according to the seventh embodiment of the present invention described in particular connection with any one of the first embodiment, the second embodiment, the fourth embodiment, the fifth embodiment, and the sixth embodiment. Reference numerals 82, 82A, 82B, 82C, 82D and 82E denote directional pattern regions of ultrasonic waves transmitted and received by the ultrasonic transmitter-receivers 81, 81A, 81B, 81C, 81D and 81E, 83 denotes a self-propelled type robot, 84A, 84B, 84C, 84D and 84E denote obstacles, 85 denotes an automobile, and 86 denotes a measurement channel.

Referring to FIG. 9A, in the ultrasonic transmitter-receiver 81A, a surface of a casing section is arranged almost flush with second surface region 8 in the vicinity of a top of the casing section of the self-propelled type robot 83. According to the ultrasonic transmitter-receiver 81A of the seventh embodiment of the present invention, the directional pattern region 82A of ultrasonic transmission and reception waves can be made almost horizontal (parallel) to a floor surface 88A and is able to perform scanning in a circumferential direction as illustrated in FIG. 9A. Therefore, obstacles in all circumferential directions of the self-propelled type robot 83 can be detected without arranging ultrasonic transmitter-receivers 81A dispersedly around the casing section or providing the casing section with a special mechanical system for directing the ultrasonic transmitter-receiver 81A toward a periphery.

In FIG. 9B, the ultrasonic transmitter-receivers 81D, 81E, 81B and 81C are arranged almost flush with a lower surface of bumper sections at front and rear ends of a body of the automobile 85 and with wall surfaces of portions near front and rear ends of a roof of the body without providing any special protrusion. Similarly to FIG. 9A, the directional pattern regions 82D, 82E, 82B and 82C of the ultrasonic waves transmitted and received can be made almost horizontal (parallel) to the ground surface 88B. Therefore, as shown in FIG. 9B, it becomes possible to detect obstacles 84D and 84E on the ground existing in blind spots in front of and behind the automobile 85, obstacles 84B and 84C of the roof such as a guardrail, signboard and the like. Moreover, it is possible to particularly provide the roof portion with no protruding portion or the like for the ultrasonic transmitter-receivers, and accordingly, there is no possibility of impairing a degree of freedom of design and so on.

In FIG. 9C, the ultrasonic transmitter-receiver 81 is arranged flush with an inner wall surface of measurement channel 86. A directional pattern region 82 of an ultrasonic wave transmitted and received is almost parallel to the channel, and transmission and reception of an ultrasonic wave are performed with opposite ultrasonic transmitter-receiver 81. In this case, there is no need to provide a concave portion or a convex portion in the channel since the ultrasonic transmitter-receiver 81 is not required to face directly, and highly accurate flow rate measurement is possible with a mobile state of fluid steadily maintained in the channel. This will be described in detail below as the eighth embodiment. There are provided a transmitter circuit 701 for driving the ultrasonic transducer 81, a receiver circuit 702 for executing amplification, band limiting and so on of an ultrasonic wave received by the other ultrasonic transducer 81, a changeover circuit 703 for changing a direction of transmission and reception, a time measuring section 704 for measuring a propagation time on the basis of an output from the receiver circuit 702, a flow rate calculating section 705 for obtaining a flow rate on the basis of an output value from the time measuring section 704, a display section 706 for displaying the flow rate calculated in the flow rate calculating section 705 and so on, and a control section 707 for controlling measurement timing and so on. Therefore, by transmitting an ultrasonic wave from one ultrasonic transducer 81 to the other ultrasonic transmitter-receiver 81 and receiving the ultrasonic wave that has passed through fluid to be measured, such as a gas, by the other ultrasonic transmitter-receiver 81, a propagation time between the ultrasonic transmitter-receivers 81 and 81 is measured by the time measuring section 704. Subsequently, conversely by transmitting an ultrasonic wave from the other ultrasonic transducer 81 to the one ultrasonic transducer 81 and receiving the ultrasonic wave that has passed through the fluid to be measured, such as a gas, by the one ultrasonic transmitter-receiver 81, the propagation time between the ultrasonic transmitter-receivers 81 and 81 is measured by the time measuring section 704. As described above, the propagation time of the ultrasonic wave between the pair of ultrasonic transducers 81 and 81 is measured a prescribed number of times, and the flow rate of the fluid to be measured, such as a gas, is calculated by the flow rate calculating section 705 on the basis of a value in the flow rate calculating section 705. Therefore, the ultrasonic transducers 81 and 81 can perform transmission and reception. In this case, a flow rate calculation system is constituted of elements from the transmitter circuit 701 to the control section 707.

Eighth Embodiment

An ultrasonic flowmeter for measuring a flow rate of a fluid by an ultrasonic wave, which is one example of application equipment of the ultrasonic transmitter-receiver as one example of the ultrasonic sensor according to an eighth embodiment of the present invention will be described with reference to FIGS. 12A through 17.

Before describing the ultrasonic flowmeter of the eighth embodiment, reference is made to a conventional ultrasonic flowmeter.

In recent years, an ultrasonic flowmeter, which measures mobile velocity of a fluid by measuring a time during which an ultrasonic wave is transmitted through a prescribed propagation path and measures a flow rate from this measured value, is being utilized for a gas meter, chemical reaction controlling, and the like.

A principle of measurement of the conventional ultrasonic flowmeter will be described below with reference to FIG. 17. In the ultrasonic flowmeter shown in FIG. 17, a fluid in a pipe is flowing at a velocity V in a direction of arrow V in FIG. 17. A pair of ultrasonic transmitter-receivers 401 and 402 are arranged oppositely to each other on pipe walls 403 of the ultrasonic flowmeter. Each of the ultrasonic transmitter-receivers 401 and 402 is provided with a transducing device (transducer) for converting electrical energy into mechanical energy and converting mechanical energy into electrical energy. This transducing device is constructed of, for example, a piezoelectric transducer of piezoelectric ceramics or the like and exhibits a resonance characteristic similarly to a piezoelectric buzzer and a piezoelectric oscillator.

Operation of the ultrasonic flowmeter will be described first in a case where the ultrasonic transmitter-receiver 401 is used as a transmitter of an ultrasonic wave and the ultrasonic transmitter-receiver 402 is used as a receiver of an ultrasonic wave.

If an AC voltage having a frequency in the vicinity of a resonance frequency of the ultrasonic transmitter-receiver 401 is applied to the piezoelectric transducer of the ultrasonic transmitter-receiver 401, then the ultrasonic transmitter-receiver 401 radiates an ultrasonic wave into fluid in the pipe. This ultrasonic wave propagates along a propagation path L1 and reaches the ultrasonic transmitter-receiver 402. The piezoelectric transducer of the ultrasonic transmitter-receiver 402 receives this ultrasonic wave and outputs a voltage signal.

Subsequently, the ultrasonic transmitter-receiver 402 is operated as a transmitter of an ultrasonic wave. In concrete, by applying an AC voltage having a frequency in the vicinity of the resonance frequency of the ultrasonic transmitter-receiver 402 to the piezoelectric transducer of the ultrasonic transmitter-receiver 402, the ultrasonic transmitter-receiver 402 radiates an ultrasonic wave into the fluid in the pipe. The ultrasonic wave propagates along a propagation path L2 and reaches the ultrasonic transmitter-receiver 401. The piezoelectric transducer of the ultrasonic transmitter-receiver 401 receives this ultrasonic wave and outputs a voltage signal.

As described above, the ultrasonic transmitter-receivers 401 and 402, which are each one ultrasonic transducer, can perform a function of a receiver and a function of a transmitter. According to this ultrasonic flowmeter, ultrasonic waves are continuously radiated from the ultrasonic transmitter-receiver when an ac voltage is continuously applied and it becomes difficult to measure a propagation time. Therefore, a burst voltage signal having a carrier of a pulse signal is normally used as a drive voltage.

If an ultrasonic burst signal is radiated from the ultrasonic transmitter-receiver 401 by applying a drive burst voltage signal to the ultrasonic transmitter-receiver 401, then this ultrasonic wave burst signal propagates through the propagation path L1 of a distance L and reaches the ultrasonic transmitter-receiver 402 after a lapse of time t.

The ultrasonic transmitter-receiver 402 can convert only an ultrasonic wave burst signal that has propagated into an electric burst signal at a high signal-to-noise ratio. An ultrasonic wave burst signal is radiated by using this electric burst signal as a trigger and applying again the drive burst voltage signal to the ultrasonic transmitter-receiver 401.

A device as described above is called a "sing-around device". Moreover, a time required for an ultrasonic pulse to reach the ultrasonic transmitter-receiver 402 from the ultrasonic transmitter-receiver 401 is called a "sing-around period", and its reciprocal is called a "sing-around frequency".

Figure 17:
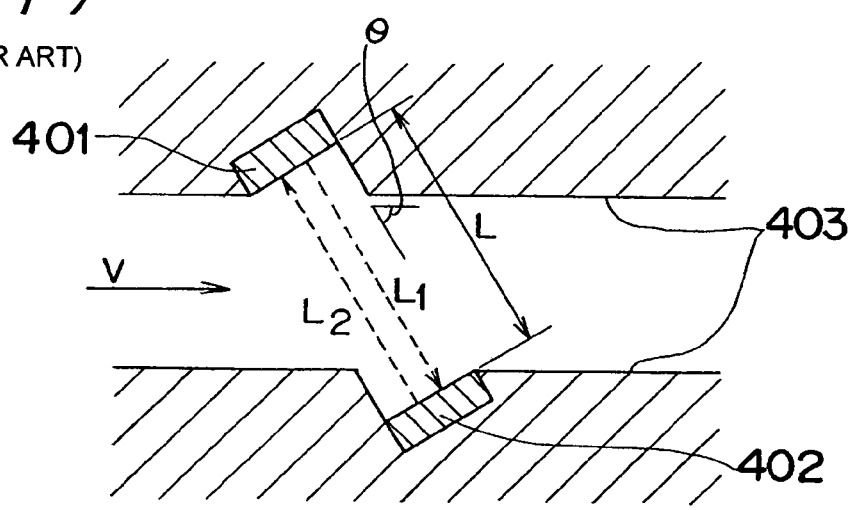
FIG. 17 is a sectional view of a conventional ultrasonic flowmeter.

It is assumed that the flow velocity of the fluid flowing in the pipe is V, a velocity of the ultrasonic wave in the fluid is C and an angle between a flow direction of the fluid, and a propagation direction of an ultrasonic pulse is θ in the ultrasonic flowmeter of FIG. 17. Further, it is assumed that a time required for the ultrasonic pulse emitted from the ultrasonic transmitter-receiver 401 to reach the ultrasonic transmitter-receiver 402 (sing-around period) is $t_1$, and the sing-around frequency is $f_1$ when the ultrasonic transmitter-receiver 401 is used as a transmitter and the ultrasonic transmitter-receiver 402 is used as a receiver. At this time, the following expression (4) holds.

$$f_1=1/t_1=(C+V\cos\theta)/L \quad (4)$$

Conversely, if it is assumed that the sing-around period is $t_2$ and the sing-around frequency is $f_2$ when the ultrasonic transmitter-receiver 402 is used as a transmitter and the ultrasonic transmitter-receiver 401 is used as a receiver, then a relationship of following expression (5) holds.

$$f_2=1/t_2=(C-V\cos\theta)/L \quad (5)$$

A frequency difference Δf between both the sing-around frequencies is expressed by the following expression (6) based on expression (4) and expression (5).

$$\Delta f=f_1-f_2=2V\cos\theta/L \quad (6)$$

As is apparent from expression (6), the flow velocity V of the fluid can be obtained from the distance L of the propagation path of the ultrasonic wave and the frequency difference Δf. Then, the flow rate can be determined from the flow velocity V.

In the ultrasonic flowmeter of FIG. 17, a matching layer (not shown) is provided on a surface of transmission and reception of an ultrasonic wave in the piezoelectric transducer of the ultrasonic transmitter-receiver. This is intended to alleviate a difference in an inherent acoustic impedance (hereinafter referred to as an "acoustic impedance") between the fluid to be measured and the piezoelectric element by a layer (matching layer) that has an intermediate acoustic impedance, and to suppress reflection of an ultrasonic wave at an interface between media that have different acoustic impedances. There occurs an inconvenience in that the ultrasonic wave emitted from the ultrasonic transmitter-receiver does not sufficiently enter the fluid to be measured when an interface of a large acoustic impedance difference exists in the propagation path of the ultrasonic wave, and this disadvantageously leads to impossible flow rate measurement or significantly reduced measurement accuracy. Therefore, in order to avoid the above inconvenience and improve measurement accuracy of the ultrasonic flowmeter, it becomes important to appropriately set an acoustic impedance of the matching layer. The acoustic impedance is generally defined by the following expression (7).

$$\text{Acoustic Impedance}=(\text{Density})\times(\text{Acoustic Velocity}) \quad (7)$$

The acoustic impedance of the piezoelectric transducer that generates ultrasonic vibrations is, for example, about $30\times10^6$ kg·m$^{-2}$·s$^{-1}$, and the acoustic impedance of air is about 400 kg·m$^{-2}$·s$^{-1}$. When measuring the flow velocity of air, it is preferable to set the acoustic impedance of the matching layer to about $0.11\times10^6$ kg·m$^{-2}$·s$^{-1}$ Conventionally, in order to form a matching layer having acoustic impedance intermediate those of the piezoelectric transducer and air, a material obtained by solidifying a material (for example, glass balloons or plastic balloons) of a comparatively small density with a resin has been used.

However, there has been a problem in that, even with the matching layer employed as described above, a propagation loss has inevitably occurred by all means and a measurement sensitivity has been reduced when propagating an ultrasonic wave from the piezoelectric transducer into a gas of air or the like. A reason why it is difficult to efficiently propagate an ultrasonic wave from a solid to a gas is that the acoustic impedance of the gas is significantly smaller than the acoustic impedance of the solid, and a strong reflection of the ultrasonic wave occurs at an interface even if the matching layer is interposed.

Moreover, in the ultrasonic flowmeter of the type shown in FIG. 17, a cavity portion for arranging an ultrasonic transmitter-receiver is necessary inside the channel of the flow measurement section, and existence of this cavity portion sometimes causes disorder of flow of the fluid to be measured. Moreover, since the flow rate itself comes to have an extremely small quantity, the channel is required to be made minute for microchemical analysis. In the above case, the conventional construction has had a problem in that the ultrasonic transmitter-receiver has been unable to be arranged in the channel and unable to be applied to the flow measurement of a minimum quantity.

The eighth embodiment of the present invention is made in view of the aforementioned problems and has an object of providing a highly sensitive ultrasonic flowmeter capable of also coping with flow measurement of an ultrasmall quantity without disordering flow inside a channel that is a flow measurement section.

The ultrasonic flowmeter of the eighth embodiment of the present invention includes a flow measurement section having an inner wall that defines a channel of fluid to be measured, at least one ultrasonic transducer that is provided outside a channel space enclosed by an inner wall of the flow measurement section and performs transmission and/or reception of an ultrasonic wave, and an ultrasonic flowmeter that is arranged between an ultrasonic transducer and the channel space and provided with a propagation medium portion that forms a propagation path of an ultrasonic wave. The density $\rho_1$ of the propagation medium portion, the acoustic velocity $C_1$ of the propagation medium portion, the density $\rho_2$ of the fluid to be measured, and the acoustic velocity $C_2$ in the fluid to be measured are constructed so as to satisfy the relationship expressed as $(\rho_2/\rho_1)<(C_1/C_2)<1$.

In a preferred embodiment, a number of the ultrasonic transducers is plural, a first ultrasonic transducer from among the plurality of ultrasonic transducers is arranged so as to emit an ultrasonic wave to a second ultrasonic transducer from among the plurality of ultrasonic transducers, and the second ultrasonic transducer is arranged so as to emit an ultrasonic wave to the first ultrasonic transducer.

In a preferred embodiment, the propagation medium portion has a first surface region that faces an ultrasonic vibration surface of an ultrasonic transducer and a second surface region that faces the channel space, and the second surface region of the propagation medium portion is inclined with respect to the first surface region.

In a preferred embodiment, the first surface region of the propagation medium portion is inclined in a direction of flow velocity of the fluid to be measured in the channel space, and the second surface region is parallel to the direction of flow velocity of the fluid to be measured in the channel space.

In a preferred embodiment, the second surface region of the propagation medium portion forms substantially no difference in level between it and the inner wall of the flow measurement section.

In a preferred embodiment, the density $\rho_1$ of the propagation medium portion, the incident angle $\theta_1$ of an ultrasonic wave relative to an interface between the propagation medium portion and the fluid to be measured, the density $\rho_2$ of the fluid to be measured, and the approach angle $\theta_2$ of the ultrasonic wave from the interface to the fluid to be measured are constructed so as to almost satisfy the relationship expressed as $\rho_2/\rho_1 = \cot\theta_2/\cot\theta_1$.

In a preferred embodiment, the fluid to be measured is a gas whose density $\rho_2$ is not greater than 10 kg·m$^{-3}$.

In a preferred embodiment, the propagation medium portion is formed of a dry gel of an inorganic oxide or an organic polymer.

In a preferred embodiment, a solid frame portion of the dry gel is made hydrophobic.

In a preferred embodiment, the dry gel has a density of not greater than 500 kg/m$^3$, and the dry gel has a mean pore diameter of not greater than 100 nm.

In a preferred embodiment, there is possessed a matching layer, which is provided between the ultrasonic transducer and the propagation medium portion and acoustically matches the ultrasonic transducer with the propagation medium portion.

In a preferred embodiment, a size of the channel space in the flow measurement section, measured in a direction perpendicular to the direction of flow velocity of the fluid to be measured, is not greater than one half of a wavelength at a central frequency of the ultrasonic wave in the fluid to be measured.

In a preferred embodiment, the ultrasonic transducer is constructed so as to form a convergence sound field.

In a preferred embodiment, the first surface region of the propagation medium portion is curved so as to form a lens surface.

The ultrasonic flowmeter of the present invention includes: a flow measurement section having an inner wall that defines a gas channel; a pair of ultrasonic transducers provided outside a channel space enclosed by the inner wall of the flow measurement section, for performing transmission and/or reception of an ultrasonic wave; and a pair of propagation medium portions arranged between each of the pair of ultrasonic transducers and the channel space, for refracting a propagation path of an ultrasonic wave. The propagation medium portion has a first surface region that faces the ultrasonic vibration surface of the ultrasonic transducer and a second surface region that faces the channel space. The first surface region of the propagation medium portion is inclined with respect to a direction of flow velocity of gas in the channel space, and the second surface region is almost parallel to the direction of flow velocity of the gas in the channel space.

The present inventors have found that an ultrasonic wave can be propagated from a solid to a fluid (particularly, gas) causing almost no loss at an interface if the ultrasonic wave is appropriately refracted by using a propagation medium portion made of an appropriate material in an ultrasonic transmitter-receiver, and come to consider the present invention.

In the ultrasonic transmitter-receiver according to the eighth embodiment of the present invention, the propagation medium portion, which has a surface (first surface region) inclined in the flow direction of the fluid to be measured and a surface (second surface region) almost parallel to the flow direction of the fluid to be measured, is arranged between the ultrasonic transducer and the fluid to be measured. The second surface region of the propagation medium portion is matched with a plane that defines the channel of the fluid so as not to disorder the flow of the fluid.

The eighth embodiment of the present invention will be described below with reference to the drawings.

Figure 12A:
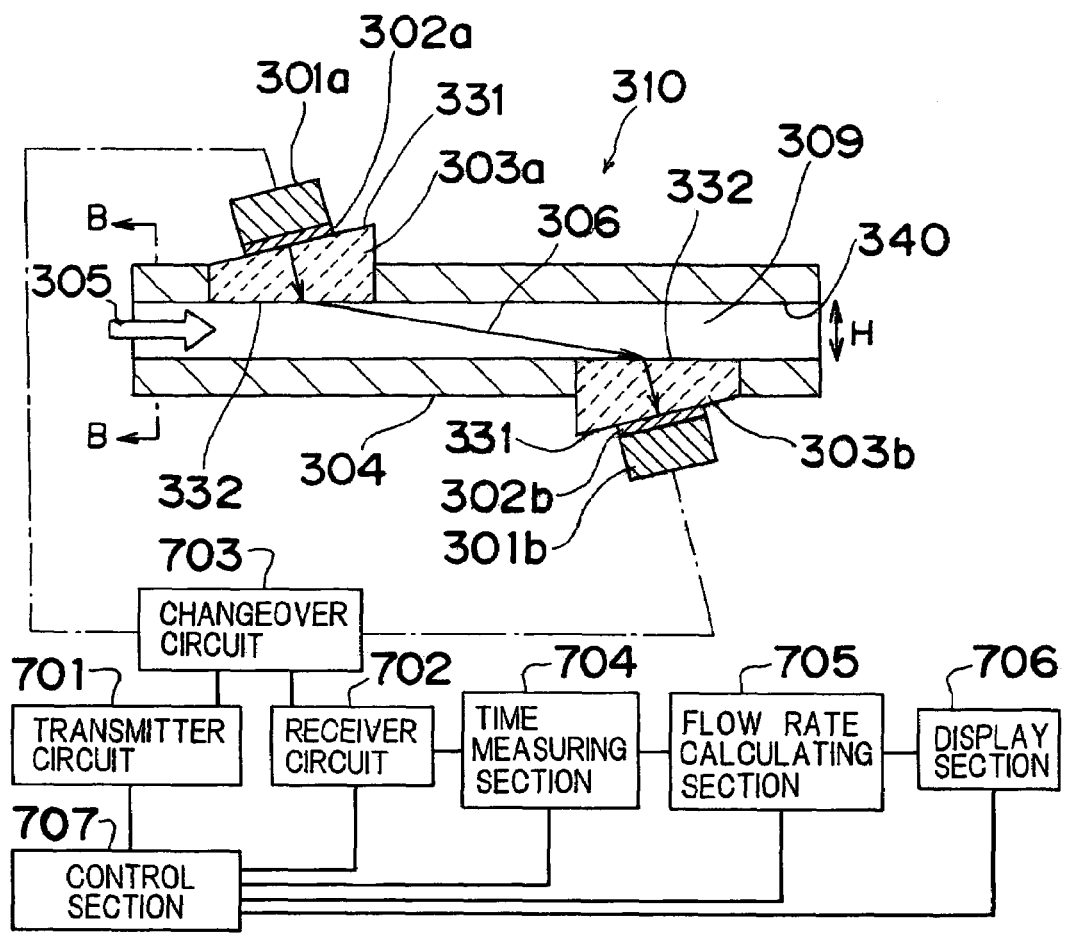
FIGS. 12A and 12B is a sectional view along a lengthwise direction of an ultrasonic flowmeter according to an eighth embodiment of the present invention, and a sectional view taken along line B—B of FIG. 12A perpendicular to the lengthwise direction of the ultrasonic flowmeter of the eighth embodiment.
Figure 12B:
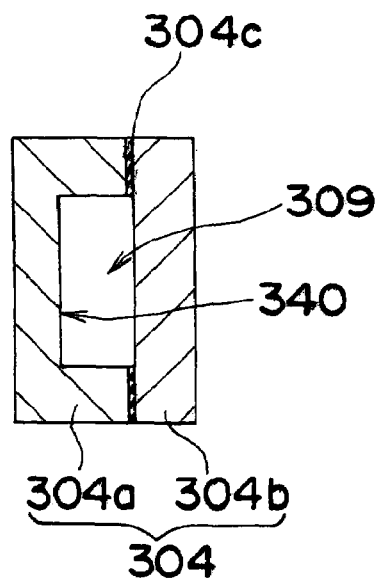

Reference is first made to the ultrasonic flowmeter of the eighth embodiment of the present invention with reference to FIGS. 12A and 12B. FIG. 12A shows a cross section along a lengthwise direction of an ultrasonic flowmeter 310 of the eighth embodiment. FIG. 12B shows a cross section taken along line B—B of FIG. 12A perpendicularly to the lengthwise direction of the ultrasonic flowmeter 310.

This illustrated ultrasonic flowmeter 310 includes: a tubular flow measurement section 304 having an inner wall 340 that defines a channel of fluid to be measured; a pair of ultrasonic transmitter-receivers (ultrasonic transducers) 301a and 301b provided outside a channel space 309 enclosed by the inner wall 340 of the flow measurement section 304, for performing transmission and/or reception of an ultrasonic wave; and propagation medium portions 303a and 303b arranged between the ultrasonic transmitter-receivers 301a and 301b and the channel space 309, for forming a propagation path of an ultrasonic wave. The fluid to be measured is assumed to flow in a direction of arrow 305 inside the channel space 309 enclosed by the inner wall 340 of the flow measurement section 304. The ultrasonic transmitter-receivers (ultrasonic transducers) 301a and 301b are any of the ultrasonic transmitter-receivers of the first through sixth embodiments. The propagation medium portions 303a and 303b correspond to the propagation medium portions 6, 6A, 6B, 6C, 6D, 6E, 6F, and 6G. It is to be noted that its casing is not shown for sake of simplicity.

In the eighth embodiment, an ultrasonic wave radiation surface of the ultrasonic transmitter-receiver 301a is inclined in the flow direction 305 of the fluid to be measured, and an ultrasonic wave emitted from the ultrasonic transmitter-receiver 301a is diagonally incident on the inner wall of the flow measurement section 304. Then, the ultrasonic wave is refracted at an interface between the propagation medium portion 303a and the fluid to be measured, and received by one ultrasonic transmitter-receiver 301b through a propagation path 306.

A section (cross section perpendicular to the flow direction 305) of the channel space 309 in the eighth embodiment is rectangular as shown in FIG. 12B. The flow measurement section 304 of the eighth embodiment is produced by solidifying the components 304a and 304b with a sealing material 304c. It is to be noted that the shape of the channel space 306 is not limited to the illustrated one and may be another shape (for example, circular).

The propagation medium portions 303a and 303b have a first surface region 331 that faces ultrasonic vibration surfaces of the ultrasonic transmitter-receivers 301a and 301b, and a second surface region 332 that faces the channel space 309. In the eighth embodiment, assuming that density of the propagation medium portions 303a and 303b is $\rho_1$, acoustic velocity of the propagation medium portions 303a and 303b is $C_1$, density of the fluid to be measured is $\rho_2$, and acoustic velocity of the fluid to be measured is $C_2$, then material of the propagation medium portions 303a and 303b is selected so that the relationship expressed by the following expression (8) is satisfied.

$$(\rho_2/\rho_1) < (C_1/C_2) < 1 \tag{8}$$

When measuring a flow rate of a gas, it is difficult to find a material that satisfies the aforementioned condition. A reason is that there are few solid materials whose acoustic velocity $C_1$ is smaller than the acoustic velocity $C_2$ of a gas. In order to provide the propagation medium portions 303a and 303b that satisfy the aforementioned condition in the eighth embodiment, the propagation medium portions 303a and 303b are formed of a dry gel of an inorganic oxide or a dry gel of an organic polymer. A solid frame portion of the dry gel employed in the eighth embodiment is made hydrophobic, and its density is not greater than 500 kg/m³. This dry gel is a nano-porous dry gel (nanoporous dry gel) having a mean pore diameter of not greater than 100 nm.

The solid frame portion of the dry gel of the inorganic oxide preferably has an ingredient of at least silicon oxide (silica) or aluminum oxide (alumina). Moreover, the solid frame portion of the dry gel of the organic polymer can be constructed of a general thermosetting resin or a thermoplastic resin. For example, there can be used polyurethane, polyurea, phenol cured resin, polyacrylamide, polymethyl methacrylate, or the like.

In a case where the propagation medium portions 303a and 303b are formed of a nanoporous dry gel that has a main ingredient of, for example, silica, if the density $\rho_1$ is 200 kg/m³, then the acoustic velocity $C_1$ can be set within a range of about 100 m/s to 180 m/s. When the fluid to be measured is air, since the density $\rho_2$ of air is 1.22 kg/m³ and the acoustic velocity $C_2$ is 340 m/s, it is possible to concurrently satisfy the relationships expressed as $\rho_2 < \rho_1$ and $C_1 < C_2$ and satisfy the relationship expressed as $(\rho_2/\rho_1) < (C_1/C_2)$ by adopting the propagation medium portions 303a and 303b. When measuring a flow rate of a gas such as natural gas, the propagation medium portions 303a and 303b preferably has a density $\rho_1$ ranging from 100 to 300 kg/m³ and an acoustic velocity $C_1$ ranging from 100 to 300 m/s.

The ultrasonic transmitter-receivers 301a and 301b have a piezoelectric element that functions as an ultrasonic transducer, and transmission and/or reception of an ultrasonic wave can be performed. As a piezoelectric element, piezoelectric ceramics are suitably employed.

In the ultrasonic flow measuring unit 310 of the eighth embodiment, a matching layer 302a is provided between the propagation medium portion 303a and the ultrasonic transmitter-receiver 301a, and a matching layer 302b is provided between a propagation medium portion 303b and an ultrasonic transmitter-receiver 301b. The matching layers 302a and 302b have functions to improve acoustic matching between piezoelectric ceramics (acoustic impedance: $30 \times 10^6$ kg·m⁻²·s⁻¹) that are ultrasonic generation sources of the ultrasonic transmitter-receivers 301a and 301b, and the propagation medium portions 303a and 303b.

When forming the propagation medium portions 303a and 303b of a nanoporous dry gel (acoustic impedance: $3 \times 10^4$ kg·m⁻²·s⁻¹) having a main ingredient of silica, by adopting matching layers 302a and 302b produced from a material of an acoustic impedance in the vicinity of $1 \times 10^6$ kg·m⁻²·s⁻¹, a propagation efficiency of ultrasonic energy can be made to be almost one and more concretely be not smaller than 0.95. The material as described above can be provided by a composite material obtained by solidifying hollow glass balls with a resin material. A thickness of the matching layers 302a and 302b is preferably set to a quarter wavelength of the ultrasonic wave used.

Figure 13:
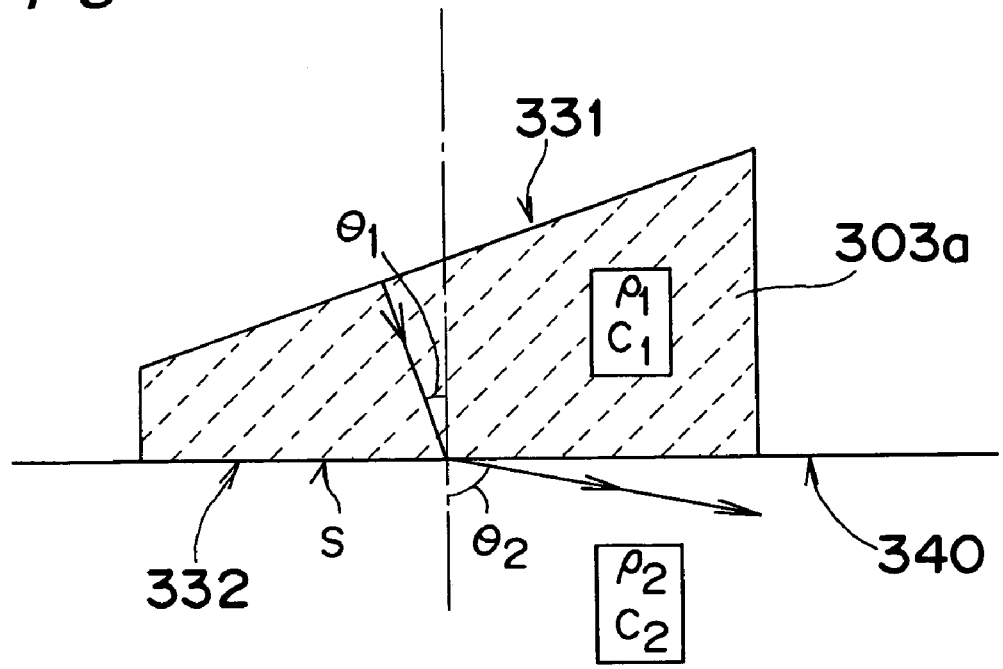
FIG. 13 is a view showing refraction of an ultrasonic wave at an interface between a propagation medium portion and a fluid to be measured.

Next, a behavior of an ultrasonic wave propagating from the propagation medium portion 303a to the fluid to be measured will be described in detail below with reference to FIG. 13.

According to the aforementioned relationship of arrangement, an ultrasonic wave enters an interface S along a direction inclined from a normal direction of the interface S between the propagation medium portion 303a and a fluid to be measured. It is assumed that an incident angle of the ultrasonic wave with respect to the normal direction of the interface is $\theta_1$ ($0° < \theta_1 < 90°$). At this time, the ultrasonic wave is refracted at the interface S between the propagation medium portion 303a and the fluid to be measured and enters the fluid to be measured at an angle (approach angle) $\theta_2$ with respect to the normal direction of the interface S ($\theta_1 < \theta_2$).

In the eighth embodiment, when $\rho_2$ of the fluid to be measured is given, various parameters ($\rho_1$, $\theta_1$, and $\theta_2$) are set so as to approximately satisfy the relationship of the following expression (9).

$$(\rho_2/\rho_1) = (\cot \theta_2 / \cot \theta_1) \tag{9}$$

With the above setting, the propagation efficiency of ultrasonic energy from the propagation medium portion 303a to the fluid to be measured becomes almost one. At this time, the incident angle $\theta_1$ satisfies the condition expressed by the following expression (10).

$$(\cot \theta_1)^2 = [(c_1/c_2)^2 - 1]/[(\rho_2/\rho_1)^2 - (c_1/c_2)^2] \tag{10}$$

Therefore, if $\rho_1$ and $C_1$ of the propagation medium portion 303a and $\rho_2$ and $C_2$ of the fluid to be measured are determined, then the incident angle $\theta_1$ is determined according to expression (10). Moreover, if the incident angle $\theta_1$ is determined, then the approach angle $\theta_2$ is determined according to expression (9).

If the incident angle $\theta_1$ and the approach angle $\theta_2$ are determined, then the inclination angle of the first surface region 331 of the propagation medium portion 303a and an interval between the two ultrasonic transmitter-receivers 301a and 301b, and so on, can also be determined.

The aforementioned fact is applied as it is when the ultrasonic wave is received.

In the eighth embodiment, by forming the propagation medium portions 303a and 303b of the aforementioned material, the acoustic velocity $C_1$ of the propagation medium portions 303a and 303b can be set to 180 m/s, and the density $\rho_1$ can be set to 200 kg/m³. When measuring a flow rate of air, the density $\rho_2$ of the fluid (air) to be measured is 1.22 kg/m³, and an acoustic velocity $C_2$ is 340 m/s. Therefore, it is proper to set the incident angle $\theta_1$ to 32° and set the approach angle $\theta_2$ to 89° according to the relationships of expression (9) and expression (10). The approach angle $\theta_2$ is close to 90°, and therefore, the ultrasonic wave in the fluid to be measured is to propagate in a direction almost parallel to the flow direction 305.

A size H (see FIG. 12A) of the channel space 309 enclosed by the inner wall 340 of the flow measurement section 304 in the eighth embodiment is preferably set to a wavelength of not greater than a half wavelength, or idealistically not greater than a quarter wavelength, of an ultrasonic wave in the fluid to be measured. By setting the size of the channel space 309 to the size as described above, appearance of a propagation mode due to acoustic wave reflection in the channel space 309 can be restrained, and time measurement accuracy can be increased. For example, when wavelength λ of the ultrasonic wave to be used is about 4 mm, the size H of the channel space 309 can be set to about 2 mm. In this case, assuming that a lowest flow velocity to be measured is 1 mm/s and measurement accuracy of the propagation time is 1 ns (nanosecond), then an interval in the transverse direction between the ultrasonic transmitter-receivers 301a and 301b can be set to about 120 mm.

According to the eighth embodiment, almost no propagation loss occurs at the interface S between the propagation medium portions 303a and 303b and the fluid to be measured, and therefore, it is not required to match their acoustic impedances at this interface S.

The propagation medium portions 303a and 303b are not required to be constructed of a material whose density $\rho_1$ and acoustic velocity $C_1$ are thoroughly uniform, and are allowed to have a laminate structure in which a plurality of kinds of material layers of varied density $\rho_1$ and acoustic velocity $C_1$ are laminated. When the laminate structure as described above is possessed, although it is sometimes a case where an ultrasonic wave does not travel straightly in the propagation medium portions 303a and 303b, there is no special problem. An important point is that the density $\rho_1$, the acoustic velocity C, and the incident angle $\theta_1$ of the propagation medium portions 303a and 303b are set so as to satisfy the aforementioned expressions in a region in the vicinity of the interface between the propagation medium portions 303a and 303b and the fluid to be measured.

Moreover, as shown in FIG. 12A, the ultrasonic flow measuring unit 310 includes: a transmitter circuit 701 for driving an ultrasonic transducer 81; a receiver circuit 702 for executing amplification, band limiting, and so on of an ultrasonic wave received by the other ultrasonic transmitter-receiver 81; a changeover circuit 703 for changing a direction of transmission and reception; a time measuring section 704 for measuring a propagation time on the basis of an output from the receiver circuit 702; a flow rate calculating section 705 for calculating a flow rate on the basis of an output value from the time measuring section 704; a display section 706 for displaying a flow rate and the like calculated in the flow rate calculating section 705; and a control section 707 for controlling the measurement timing and the like. Therefore, by transmitting an ultrasonic wave from one ultrasonic transducer 301a or 301b to the other ultrasonic transmitter-receiver 301b or 301a and receiving the ultrasonic wave that has passed through the fluid to be measured, such as a gas, by the other ultrasonic transmitter-receiver 301a or 301b, the propagation time between the ultrasonic transducers 301a and 301b is measured by the time measuring section 704. Next, by transmitting an ultrasonic wave from transducer 301b to ultrasonic transducer 301a and receiving the ultrasonic wave that has passed through the fluid to be measured, such as a gas, by the ultrasonic transducer 301a, a propagation time between the ultrasonic transducers 301a and 301b is measured by the time measuring section 704. As described above, the propagation time of an ultrasonic wave between the pair of ultrasonic transducers 301a and 301b is measured a prescribed number of times, and the flow rate of the fluid to be measured, such as a gas, is calculated by the flow rate calculating section 705 on the basis of the value in the flow rate calculating section 705. Therefore, the ultrasonic transducers 301a and 301b can perform transmission and reception. In this case, a flow rate calculation system is constituted of elements from the transmitter circuit 701 to the control section 707.

Operation of the ultrasonic flowmeter of the eighth embodiment will be described next.

First of all, an AC voltage having a frequency in the vicinity of a resonance frequency (for example, about 100 kHz to 1 MHz) is applied from the transmitter circuit 701 that concurrently serves as the drive circuit of FIG. 12B to the ultrasonic transmitter 301a. By this operation, the ultrasonic transmitter-receiver 301a radiates an ultrasonic wave on a condition of an efficiency of almost one to the propagation medium portion 303a through the matching layer 302a.

The acoustic wave, which has propagated through the medium portion 303a, is refracted at the interface between the propagation medium portion 303a and the channel space 309, radiated in the channel space 309 with an efficiency of almost one, and propagated through an inside of the fluid to be measured. Subsequently, the ultrasonic wave reaches the ultrasonic transmitter-receiver 301b through the propagation medium portion 303b and the matching layer 302b provided on an opposite side. The ultrasonic transmitter-receiver 301b converts this received ultrasonic wave into a voltage to generate a voltage signal (electric signal). A method for measuring a propagation time of the ultrasonic wave by the flow rate calculating section 705 on the basis of this electric signal and converting the flow velocity into the flow rate is similar to that of the prior art. A structural example of the drive circuit is described in Japanese Unexamined Patent Publication No. 2000-298045 and Japanese Unexamined Patent Publication No. 2000-298047.

According to the eighth embodiment, there are provided the propagation medium portions 303a and 303b that exhibit appropriate density $\rho_1$ and acoustic velocity $C_1$, and the ultrasonic wave is refracted at an appropriate angle. Therefore, propagation loss at an interface of substances can be made almost zero, and flow measurement can be achieved at a satisfactory signal-to-noise ratio. Then, according to the eighth embodiment, a flow rate of a gas (for example, hydrogen gas), of which measurement has been extremely difficult by the conventional ultrasonic flowmeter, can easily be measured.

Furthermore, according to the eighth embodiment, there is existing neither large unevenness nor difference in level, which may cause a disorder of flow, inside the channel space 309 of the flow measurement section 304, and extremely stable flow measurement becomes possible. Moreover, since the ultrasonic transmitter-receivers are arranged outside the channel space 309, a size of the channel space 309 can be arbitrarily designed not depending on sizes of the ultrasonic transmitter-receivers. As a result, the size of the channel space 309 is reduced to allow flow measurement of an ultrasmall quantity to be performed.

Ninth Embodiment

Figure 14:
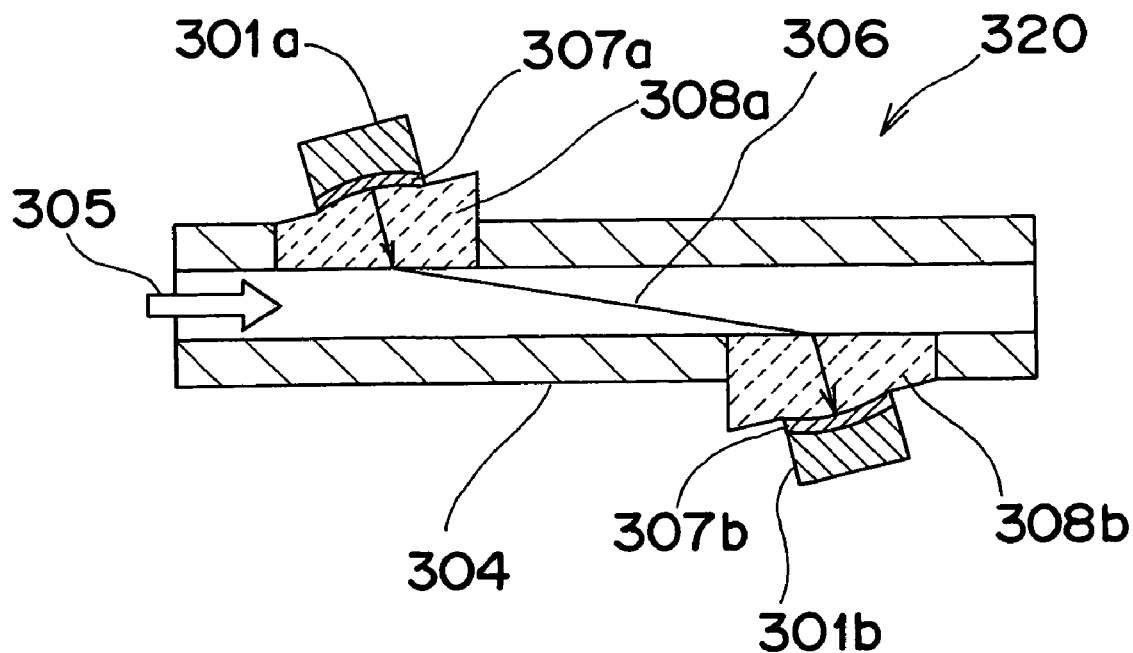
FIG. 14 is a sectional view of an ultrasonic flowmeter according to a ninth embodiment of the present invention.

An ultrasonic flowmeter as one example of the ultrasonic sensor according to a ninth embodiment of the present invention will be described with reference to FIG. 14. FIG. 14 shows a cross section along a lengthwise direction of an ultrasonic flowmeter 320 of the ninth embodiment. Like reference numerals are given to common members of the ninth embodiment and the aforementioned eighth embodiment.

Hereinafter, characteristic points of the ultrasonic transmitter-receiver 320 of the ninth embodiment will be described below, and no description is provided for portions similar to those of the ultrasonic flowmeter 310 of the eighth embodiment.

In the ultrasonic flowmeter 320 of the ninth embodiment, ultrasonic transmitter-receivers 301a and 301b are constructed so as to form a convergence sound field. In concrete, a first surface region of propagation medium portions 308a and 308b are curved so as to form a lens surface. With this arrangement, a matching layer has a concave type surface on a measured fluid side. With the above construction, an ultrasonic wave transmitted from an ultrasonic transmitter-receiver 301a is to converge inside a propagation medium portion 308a. This convergence effect enables transmission and reception of an ultrasonic wave with a larger sound pressure by use of an ultrasonic transducer of identical capability, and therefore, a signal-to-noise ratio can be further improved.

Figure 15A:
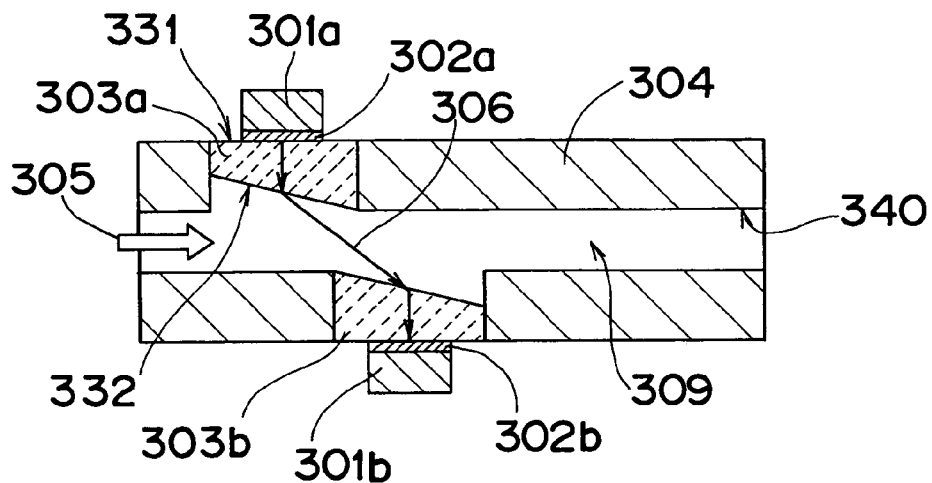
FIGS. 15A, 15B, and 15C are sectional views of an ultrasonic flowmeter according to a modification example of the eighth and ninth embodiments of the present invention.
Figure 15B:
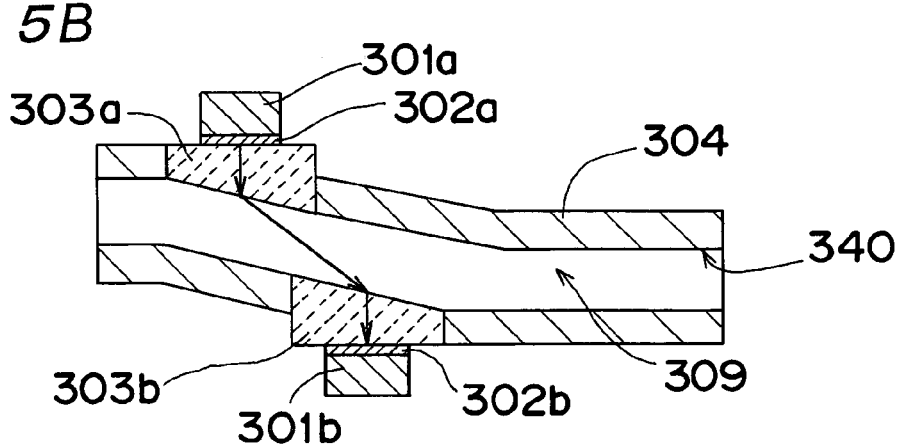
Figure 15C:
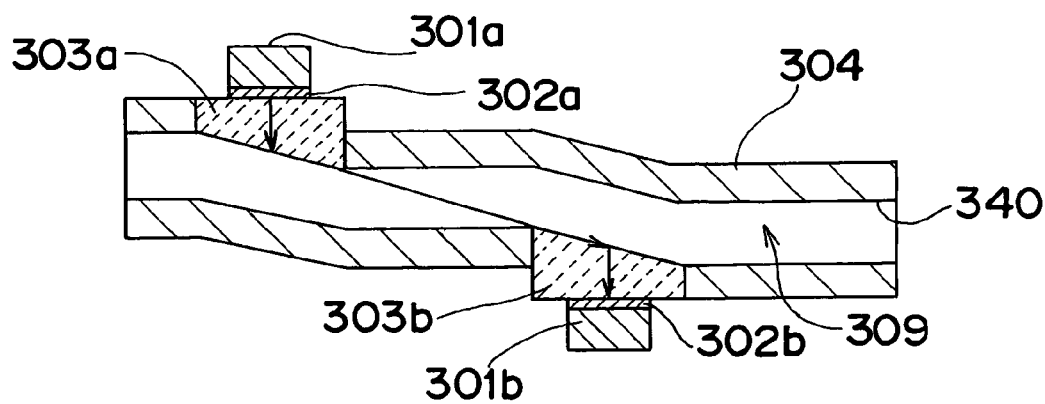

In each of the eighth and ninth embodiments described above, a first surface region 331 of the propagation medium portion is inclined in the flow velocity direction 305 of the fluid to be measured in the channel space 309, and the second surface region 332 is parallel to the flow velocity direction 305 of the fluid to be measured in the channel space 309. However, the present invention is not limited to the above construction. For example, as shown in FIG. 15A, it is acceptable to adopt a construction in which the second surface region 332 of the propagation medium portions 303a and 303b is inclined in the flow velocity direction 305 of the fluid to be measured in the channel space 309. According to the above construction, an interval between the two ultrasonic transmitter-receivers can be reduced. However, in the construction of FIG. 15A, a difference in level is formed between inner wall 340 of flow measurement section 304 and the second surface region 332 of the propagation medium portions 303a and 303b. In order to reduce or eliminate this difference in level, as shown in, for example, FIGS. 15B and 15C, it is proper to form an inclined surface in a part of the inner wall 340 of the flow measurement section 304 and make the inclined surface match with the second surface region 332 of the propagation medium portions 303a and 303b.

Figure 16A:
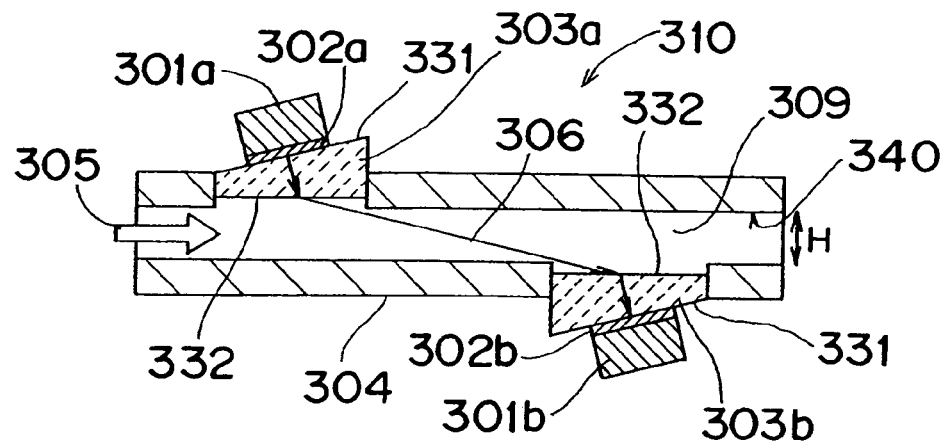
FIGS. 16A and 16B are sectional views of an ultrasonic flowmeter according to another modification example of the eighth and ninth embodiments of the present invention.
Figure 16B:
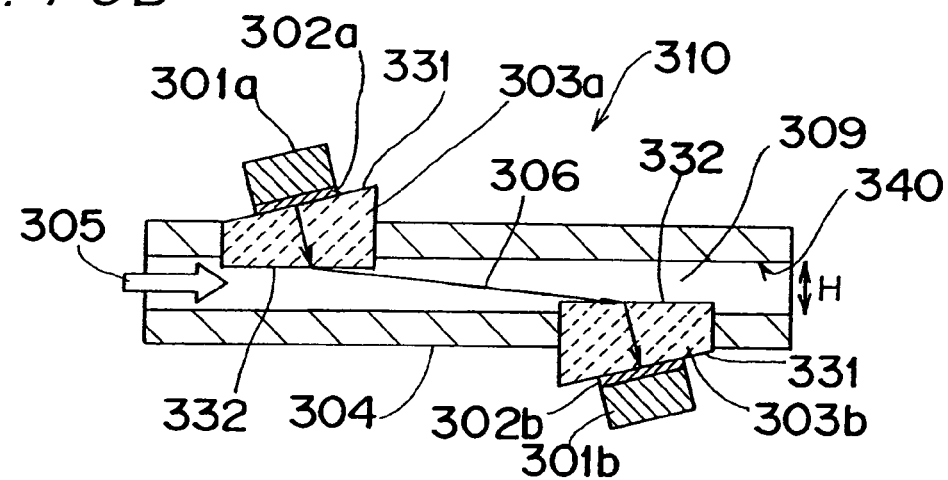

The second surface region 332 of the propagation medium portions 303a and 303b preferably has no substantial difference in level between it and the inner wall 340 of the flow measurement section 304. However, when a disorder of flow does not pose a major problem, there may exist a difference in level or unevenness as shown in FIGS. 16A and 16B.

In each of the aforementioned eighth and ninth embodiments, one pair of ultrasonic transmitter-receivers has a substantially identical construction, and an arrangement rotationally symmetrical at an angle of 180° is adopted. However, the present invention is not limited to the above construction. It is acceptable to apply the construction of the eighth and ninth embodiments to one of the one pair of ultrasonic transmitter-receivers and give a different construction (for example, the construction shown in FIGS. 15A through 15C) to the other ultrasonic transmitter-receiver. Moreover, in the eighth and ninth embodiments, not only transmission but also reception of an ultrasonic wave are performed by an identical ultrasonic transducer by employing an ultrasonic transducer as an ultrasonic transmitter-receiver. However, the eighth and ninth embodiments of the present invention are not limited to the above construction. It is acceptable to employ separate ultrasonic transducers for wave transmission and wave reception.

According to the eighth and ninth embodiments of the present invention, loss in propagating an ultrasonic wave into the fluid to be measured can be reduced to almost zero, and therefore, a flow rate of various fluids including a gas can be measured with high sensitivity.

Moreover, according to the eighth and ninth embodiments of the present invention, there is no need to provide a difference in level or unevenness inside the channel, and therefore, the embodiments can also cope with a flow measurement of an extremely small quantity without disordering flow of the fluid to be measured.

According to the present invention, there are provided the ultrasonic transducer for performing transmission and/or reception of an ultrasonic wave and the propagation medium portion that forms a propagation path of an ultrasonic wave. By appropriately setting a mutual relationship between the density $\rho_1$ and the acoustic velocity $C_1$ of the propagation medium portion and the density $\rho_2$ and the acoustic velocity $C_2$ of the fluid that fills the circumjacent space and appropriately refracting the ultrasonic wave at an appropriate angle, loss in radiating an ultrasonic wave into the fluid that fills the circumjacent space can be reduced to almost zero, and/or loss in receiving the ultrasonic wave entering from the fluid that fills the circumjacent space can be reduced to almost zero. Therefore, highly efficient wave transmission and reception become possible for various fluids including a gas. Moreover, when the fluid is a gas, wave transmission and reception can be performed almost horizontally (parallel) with respect to a wave transmission and reception surface of the ultrasonic transmitter-receiver, and the present invention can be used for developing a variety of applications.

By properly combining arbitrary embodiments of the aforementioned various embodiments, effects possessed by them can be produced.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The invention claimed is:

1. An ultrasonic sensor for performing transmission or reception of an ultrasonic wave to or from a circumjacent space filled with a fluid, comprising:
   an ultrasonic transducer; and
   a propagation medium portion, between said ultrasonic transducer and the circumjacent space, for forming a propagation path of the ultrasonic wave,
   wherein a density $\rho_1$ of said propagation medium portion, an acoustic velocity $C_1$ obtainable in said propagation medium portion, a density $\rho_2$ of the fluid that fills the circumjacent space, and an acoustic velocity $C_2$ obtainable in the fluid that fills the circumjacent space satisfy a relation expressed as $(\rho_2/\rho_1)<(C_1/C_2)<1$.

2. The ultrasonic sensor according to claim 1, wherein said propagation medium portion has a first surface region that faces an ultrasonic vibration surface of said ultrasonic transducer, and a second surface region that faces the fluid that fills the circumjacent space, with said second surface region being inclined relative to said first surface region.

3. An ultrasonic sensor for performing transmission or reception of an ultrasonic wave to or from a circumjacent space filled with a fluid, comprising:
an ultrasonic transducer;
a propagation medium portion, between said ultrasonic transducer and the circumjacent space, for forming a propagation path of the ultrasonic wave; and
a reflector in contact with said propagation medium portion for controlling the propagation path of the ultrasonic wave,
wherein a density $\rho_1$ of said propagation medium portion, an acoustic velocity $C_1$ obtainable in said propagation medium portion, a density $\rho_2$ of the fluid that fills the circumjacent space, and an acoustic velocity $C_2$ obtainable in the fluid that fills the circumjacent space satisfy a relation expressed as $(\rho_2/\rho_1)<(C_1/C_2)<1$.

4. An ultrasonic sensor for performing transmission or reception of an ultrasonic wave to or from a circumjacent space filled with a fluid, comprising:
an ultrasonic transducer;
a propagation medium portion, between said ultrasonic transducer and the circumjacent space, for forming a propagation path of the ultrasonic wave; and
a reflector in contact with said propagation medium portion for controlling the propagation path of the ultrasonic wave,
wherein a density $\rho_1$ of said propagation medium portion, an acoustic velocity $C_1$ obtainable in said propagation medium portion, a density $\rho_2$ of the fluid that fills the circumjacent space, and an acoustic velocity $C_2$ obtainable in the fluid that fills the circumjacent space satisfy a relation expressed as $(\rho_2/\rho_1)<(C_1/C_2)<1$, and
wherein said propagation medium portion has a first surface region that faces an ultrasonic vibration surface of said ultrasonic transducer, a second surface region that faces the fluid that fills the circumjacent space, and at least one third surface region between said first surface region and said second surface region in the propagation path of the ultrasonic wave and in contact with said reflector, with said second surface region being inclined with respect to at least one of said first surface region and said at least one third surface region.

5. The ultrasonic sensor according to claim 4, wherein a direction of the transmission or reception of the ultrasonic wave is almost parallel to said second surface region.

6. An ultrasonic sensor for performing transmission or reception of an ultrasonic wave to or from a circumjacent space filled with a fluid, comprising:
an ultrasonic transducer; and
a propagation medium portion, filled in a space between said ultrasonic transducer and the circumjacent space, for forming a propagation path of the ultrasonic wave,
wherein a density $\rho_1$ of said propagation medium portion, an incident angle $\theta_1$ of the ultrasonic wave relative to a direction that is normal to an interface between said propagation medium portion and the fluid that fills the circumjacent space, a density $\rho_2$ of the fluid that fills the circumjacent space, and an approach angle $\theta_2$ of the ultrasonic wave relative to the direction that is normal to the interface almost satisfy a relation expressed as $\rho_2/\rho_1 = \cot\theta_2/\cot\theta_1$.

7. The ultrasonic sensor according to claim 6, wherein said propagation medium portion comprises one of an organic polymer and a dry gel.

8. The ultrasonic sensor according to claim 7, wherein a solid frame portion of said dry gel is hydrophobic.

9. The ultrasonic sensor according to claim 7, wherein a density of said dry gel is not greater than 500 kg/m³, and a mean pore diameter of said dry gel is not greater than 100 nm.

10. The ultrasonic sensor according to claim 1, further comprising:
an acoustic matching layer, between said ultrasonic transducer and said propagation medium portion, for acoustically matching said ultrasonic transducer with said propagation medium portion.

11. The ultrasonic sensor according to claim 6, wherein the fluid that fills the circumjacent space is a gas, with the density $\rho_2$ being no greater than 10 kg/m³.

12. An ultrasonic flowmeter comprising:
a flow measurement section having an inner wall that defines a channel for a fluid to be measured;
an ultrasonic transducer provided outside said channel for performing transmission or reception of an ultrasonic wave; and
a propagation medium portion between said ultrasonic transducer and said channel for forming a propagation path of the ultrasonic wave,
wherein a density $\rho_1$ of said propagation medium portion, an acoustic velocity $C_1$ obtainable in said propagation medium portion, a density $\rho_2$ of the fluid to be measured, and an acoustic velocity $C_2$ obtainable in the fluid to be measured satisfy a relation expressed as $(\rho_2/\rho_1)<(C_1/C_2)<1$.

13. The ultrasonic flowmeter according to claim 12, further comprising:
another ultrasonic transducer provided outside said channel for performing transmission or reception of the ultrasonic wave; and
another propagation medium portion between said another ultrasonic transducer and said channel for forming a propagation path of the ultrasonic wave,
wherein a density $\rho_1$ of said another propagation medium portion, an acoustic velocity $C_1$ obtainable in said another propagation medium portion, the density $\rho_2$ of the fluid to be measured, and the acoustic velocity $C_2$ obtainable in the fluid to be measured satisfy the relation expressed as $(\rho_2/\rho_1)<(C_1/C_2)<1$,
with said ultrasonic transducer being arranged so as to emit an ultrasonic wave to said another ultrasonic transducer, and with said another ultrasonic transducer being arranged so as to emit an ultrasonic wave to said ultrasonic transducer.

14. The ultrasonic flowmeter according to claim 12, wherein
said propagation medium portion has a first surface region that faces an ultrasonic vibration surface of said ultrasonic transducer, and a second surface region that faces said channel, with said second surface region being inclined relative to said first surface region.

15. The ultrasonic flowmeter according to claim 14, wherein
said first surface region is inclined in a direction of flow velocity of the fluid to be measured in said channel, and said second surface region is parallel to the direction of flow velocity of the fluid to be measured in said channel.

16. The ultrasonic flowmeter according to claim 14, wherein
said second surface region forms substantially no difference in level between said second surface region and said inner wall of said flow measurement section.

17. The ultrasonic flowmeter according to claim 12, wherein
said propagation medium portion comprises one of an organic polymer and a dry gel of an inorganic oxide.

18. The ultrasonic flowmeter according to claim 17, wherein
a solid frame portion of said dry gel is hydrophobic.

19. The ultrasonic flowmeter according to claim 18, wherein
a density of said dry gel is not greater than 500 kg/m$^3$, and a mean pore diameter of said dry gel is not greater than 100 nm.

20. The ultrasonic flowmeter according to claim 12, wherein
the fluid to be measured is a gas, with the density $\rho_2$ being no greater than 10 kg·m$^{-3}$.

21. The ultrasonic flowmeter according to claim 12, further comprising:
an acoustic matching layer, between said ultrasonic transducer and said propagation medium portion, for acoustically matching said ultrasonic transducer with said propagation medium portion.

22. The ultrasonic flowmeter according to claim 12, wherein
a size of said channel, measured in a direction perpendicular to a direction of flow velocity of the fluid to be measured, is not greater than a half wavelength of the ultrasonic wave at a central frequency in the fluid to be measured.

23. The ultrasonic flowmeter according to claim 12, wherein
said ultrasonic transducer is to form a convergence sound field.

24. An apparatus comprising:
the ultrasonic flowmeter as recited in claim 12;
a pipe for supplying the fluid to be measured to said ultrasonic flowmeter; and
a display section for displaying a flow rate as measured by said ultrasonic flowmeter.

25. An ultrasonic flowmeter comprising:
a flow measurement section having an inner wall that defines a channel for a fluid to be measured;
an ultrasonic transducer provided outside said channel for performing transmission or reception of an ultrasonic wave; and
a propagation medium portion between said ultrasonic transducer and said channel for forming a propagation path of the ultrasonic wave,
wherein a density $\rho_1$ of said propagation medium portion, an acoustic velocity $C_1$ obtainable in said propagation medium portion, a density $\rho_2$ of the fluid to be measured, and an acoustic velocity $C_2$ obtainable in the fluid to be measured satisfy a relation expressed as $(\rho_2/\rho_1)<(C_1/C_2)<1$, and
wherein the density $\rho_1$ of said propagation medium portion, an incident angle $\theta_1$ of the ultrasonic wave relative to a direction normal to an interface between said propagation medium portion and the fluid to be measured, the density $\rho_2$ of the fluid to be measured, and an approach angle $\theta_2$ of the ultrasonic wave relative to the direction normal to the interface almost satisfy a relation expressed as $\rho_2/\rho_1 = \cot\theta_2/\cot\theta_1$.

26. An ultrasonic flowmeter comprising:
a flow measurement section having an inner wall that defines a channel for a fluid to be measured, with a size of said channel, measured in a direction perpendicular to a direction of flow velocity of the fluid to be measured, is not greater than a half wavelength of an ultrasonic wave at a central frequency in the fluid to be measured;
an ultrasonic transducer provided outside said channel for performing transmission or reception of the ultrasonic wave; and
a propagation medium portion between said ultrasonic transducer and said channel for forming a propagation path of the ultrasonic wave, with a first surface region of said propagation medium portion being curved so as to form a lens surface,
wherein a density $\rho_1$ of said propagation medium portion, an acoustic velocity $C_1$ obtainable in said propagation medium portion, a density $\rho_2$ of the fluid to be measured, and an acoustic velocity $C_2$ obtainable in the fluid to be measured satisfy a relation expressed as $(\rho_2/\rho_1)<(C_1/C_2)<1$.

27. An ultrasonic flowmeter comprising:
a flow measurement section having an inner wall that defines a channel for a gas;
a first ultrasonic transducer provided outside said channel for performing transmission or reception of an ultrasonic wave;
a first propagation medium portion between said first ultrasonic transducer and said channel for refracting a propagation path of the ultrasonic wave, said first propagation medium portion including a first surface region that faces an ultrasonic vibration surface of said first ultrasonic transducer and a second surface region that faces said channel, with said first surface region being inclined in a direction of flow velocity of the gas in said channel, and with said second surface region being almost parallel to the direction of flow velocity of the gas in said channel;
a second ultrasonic transducer provided outside said channel for performing transmission or reception of the ultrasonic wave; and
a second propagation medium portion between said second ultrasonic transducer and said channel for refracting a propagation path of the ultrasonic wave, said second propagation medium portion including a third surface region that faces an ultrasonic vibration surface of said second ultrasonic transducer and a fourth surface region that faces said channel, with said third surface region being inclined in the direction of flow velocity of the gas in said channel, and with said fourth surface region being almost parallel to the direction of flow velocity of the gas in said channel.

28. The ultrasonic flowmeter according to claim 27, wherein
a density $\rho_1$ of said first propagation medium portion and said second propagation medium portion, an acoustic velocity $C_1$ obtainable in said first propagation medium portion and said second propagation medium portion, a density $\rho_2$ of the gas, and an acoustic velocity $C_2$ obtainable in the gas satisfy a relation expressed as $(\rho_2/\rho_2)<(C_1/C_2)<1$.

29. An ultrasonic sensor for performing transmission or reception of an ultrasonic wave to or from a circumjacent space filled with a fluid, comprising:
an ultrasonic transducer; and
a propagation medium portion filled in a space between said ultrasonic transducer and the circumjacent space, for forming a propagation path of the ultrasonic wave, said propagation medium portion having a first surface region that faces an ultrasonic vibration surface of said ultrasonic transducer and a second surface region that faces the fluid filling the circumjacent space, with said second surface region being inclined relative to said first surface region.

30. The ultrasonic sensor according to claim 29, wherein a density $\rho_1$ of said propagation medium portion, an acoustic velocity $C_1$ obtainable in said propagation medium portion, a density $\rho_2$ of the fluid that fills the circumjacent space, and an acoustic velocity $C_2$ obtainable in the fluid that fills the circumjacent space satisfy a relation expressed as $(\rho_2/\rho_1)<(C_1/C_2)<1$.

* * * * *